United States Patent [19]

Cournoyer et al.

[11] 4,429,142
[45] Jan. 31, 1984

[54] XANTHENE COMPOUNDS

[75] Inventors: Richard L. Cournoyer, Waltham; James W. Foley, Andover, both of Mass.

[73] Assignee: Polaroid Corporation, Cambridge, Mass.

[21] Appl. No.: 281,981

[22] Filed: Jul. 10, 1981

Related U.S. Application Data

[60] Division of Ser. No. 169,834, Jul. 17, 1980, Pat. No. 4,304,834, which is a continuation-in-part of Ser. No. 106,901, Dec. 26, 1979, abandoned.

[51] Int. Cl.³ .......................................... C07D 311/82
[52] U.S. Cl. .................................................. 549/394
[58] Field of Search ........................................ 549/394

[56] References Cited

U.S. PATENT DOCUMENTS 4,290,955 9/1981 Cinotta et al. ...................... 549/394

Primary Examiner—Henry R. Jiles
Assistant Examiner—Robert C. Whittenbaugh
Attorney, Agent, or Firm—Sybil A. Campbell

[57] ABSTRACT

In one embodiment, the present invention is concerned with novel xanthene compounds selected from those of the formulae

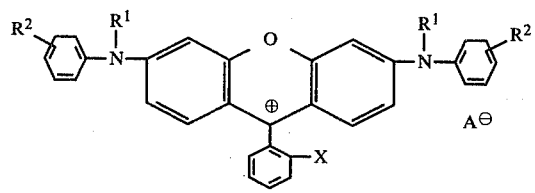

and

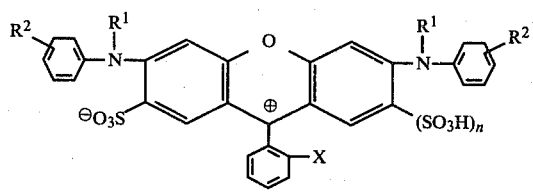

wherein each $R^1$ the same or different is alkyl, each $R^2$ the same or different is an electron-withdrawing group having a positive sigma value greater than 0.6, X is

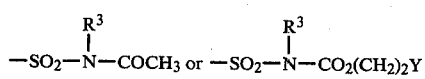

wherein $R^3$ is alkyl, Y is an electron-withdrawing group, n is 0 or 1 and A is an anion. In another embodiment, the present invention is concerned with photographic products and processes employing these xanthene compounds, e.g., as photographic light-screening dyes.

9 Claims, 2 Drawing Figures

XANTHENE COMPOUNDS

CROSS-REFERENCE TO RELATED PATENT APPLICATION

This application is a division of application Ser. No. 169,834, filed July 17, 1980, now U.S. Pat. No. 4,304,834 which, in turn, is a continuation-in-part of U.S. patent application Ser. No. 106,901 filed Dec. 26, 1979 now abandoned.

BACKGROUND OF THE INVENTION

1. Field of the Invention

This invention relates to novel xanthene compounds and to their use, e.g., as light-screening dyes in photographic products and processes.

2. Description of the Prior Art

It is well known that photographic film, and especially multicolor films, may and generally do vary from lot to lot, notwithstanding efforts to "repeat" previous films. Manufacturers of multicolor photographic films have developed a number of procedures to minimize the effects upon the final multicolor image of unavoidable variations in the manufacturing operations. These variations are reflected primarily in shifts in color balance as reflected in mismatching of the D log E curves of the individual red, green and blue exposures. Equipment used to coat multicolor films is highly precise but variations between intended coverage of silver halide and/or the dye image-forming materials do occur. Repeat batches of silver halide emulsions may, and usually do, vary in their photographic response. Individual layers may be dried to slightly different degrees. Films are stored for a period of time after coating to allow the films to "age", so that changes in sensitometry following coating have an opportunity to reach a plateau prior to sale. If the film is designed to be developed by a photofinisher or in a darkroom, processing of the exposed multicolor film is controlled within very narrow limits, typically within plus or minus a half degree of a prescribed temperature, in order to minimize sensitometric variations from film to film. Where the multicolor film is of the negative type, an opportunity to adjust the sensitometry occurs in printing the desired final positive image, during which operation the printing exposure may be appropriately color filtered.

The basic sources of sensitometric variations noted above exist also in multicolor diffusion transfer films, with the added complication that once the film is shipped, the sensitometric properties are essentially fixed. The opportunity for adjustment provided in darkroom processing, practically speaking, is unavailable for users of self-developing films. While professional and advanced amateur photographers may be skillful enough to utilize color correction filters to at least partially "rebalance" the color balance, ordinary users of the film would only be confused by such additional operations.

It is well known to use light-screening dyes in photographic elements. Such a dye may be incorporated as a filter dye in a light-sensitive emulsion layer(s) or in a layer coated over one or more light-sensitive emulsion layers or between two differently color-sensitized emulsion layers to modify the light record in the emulsion layer or to control the spectral composition of light falling on the underlying light-sensitive layer, or it may be incorporated as an anti-halation dye in a non-light-sensitive layer positioned on either side of a support carrying the light-sensitive layer(s).

The dyes employed for these purposes, in addition to having the requisite spectral absorption characteristics for their intended use, should be photochemically inert, that is, they should not have any adverse effect on the properties of the light-sensitive emulsion layer(s), and also, they should be capable of being decolorized or removed during photographic processing so as not to leave stain in the processed photographic element. In photographic processes where the dye is removed by being dissolved in a processing solution, it is usually preferred that the dye also decolorize in order to avoid contamination of the processing solution and to prevent staining from residual dye in the processed light-sensitive element.

Though various classes of dyes have been proposed for use in antihalation and color correction filter layers, the dyes heretofore employed have not been altogether satisfactory. Some of the dyes tend to reduce sensitivity, fog or exert other adverse effect on the light-sensitive material. However, the major drawback of previously employed dyes is their tendency to cause stain due to incomplete decolorization or reversal of some of the decolorized form to the original colored form. For example, some classes of dyes rely on the presence of a reagent, such as, a sulfate for "bleaching", i.e., decolorization and unless the dyes are removed from the light-sensitive material during or after processing, their color may reappear in time.

Among the classes of light-screening dyes used previously are the triarylmethane and xanthenes. For example, U.S. Pat. Nos. 1,879,537; 1,994,876; 2,350,090 and 3,005,711 disclose the use of fuchsone-type dyes in antihalation layers, and U.S. Pat. Nos. 3,406,069 and 3,615,548 are concerned with the metal chelates of fuchsone dyes as antihalation dyes. These and other types of triarylmethane dyes suffer from one or more of the drawbacks discussed above, and in particular, prior dyes of this type have been difficult to keep decolorized at the pH's normally encountered during processing subsequent to "bleaching" and in the final product. Xanthenes have been employed in antihalation layers that are removed during photographic processing. For example, U.S. Pat. Nos. 2,182,794; 2,203,767 and 2,203,768 disclose the use of rhodamine dyes in certain antihalation layers that are removed during processing in an acid bath or a plain water rinse bath depending upon the solubility characteristics of the particular layer.

Copending U.S. patent application Ser. No. 106,520 of James W. Foley filed Dec. 26, 1979 is concerned with colored triarylmethane compounds possessing in their triaryl structure a 4'-oxo-1'-naphthylidene/-phenylidene moiety, a naphthyl/phenyl moiety and a phenyl moiety substituted in the position ortho to the central carbon atom with a group that undergoes an irreversible cleavage reaction in base to provide a moiety that adds to the central carbon atom to form a new ring-closed compound which is colorless. As disclosed and claimed therein, these compounds are useful as photographic light-screening dyes which offer advantages over prior light-screening dyes because of their ability to decolorize completely and irreversibly to a substantially inert colorless product.

The present invention is concerned with another class of compounds, namely, xanthene compounds which also find utility as photographic light-screening dyes and which also are free from the deficiencies associated with the dyes previously used for this purpose. The subject dyes, which will be defined with greater particularity hereinafter, are efficient absorbers of radiation within a predetermined range in the visible range of 400 to 700 nm, may be incorporated in gelatin or other processing composition-permeable colloidal binding agents and are decolorized at an alkaline pH to yield a colorless product. Because of their ability to decolorize completely and irreversibly in base without requiring an additional reagent, such as, a sulfite for the "bleaching" reaction and because the new colorless product produced upon irreversible cleavage remains colorless in aqueous solution over a pH range of about 4.5 to 14, the cleavage product normally may be retained in the photographic light-sensitive element without the possibility of color reappearing in time. Besides being non-staining, the compounds usually are substantially inert with respect to the light-sensitive material and thus, may be positioned in a layer adjacent to a silver halide emulsion layer or directly incorporated into an emulsion layer without having any adverse effect on the properties of the emulsion.

Xanthenes of the structure

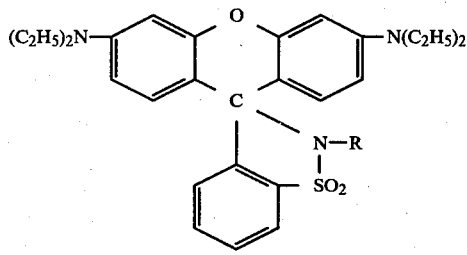

wherein R is H or —COCH$_3$ are disclosed in Beilstein's Handbuch der Organischen Chemie, Vol. 27, p. 534. These compounds are synthesized by condensing m-diethylaminophenol with saccharin at a temperature of 165° C. to give the compound wherein R is H, which compound is then heated to boiling with acetic acid anhydride to yield the N-acylated derivative. As reported therein, solutions of the N-acetyl compound unlike solutions of the N-unsubstituted compound (R=H) are not decolorized by boiling, and the acetyl group splits off only after prolonged boiling with alcoholic sodium hydroxide. Further to the N-unsubstituted compound, it has been found that this compound is colorless at an alkaline pH, faintly colored at neutrality and becomes more intensely colored as the pH is reduced.

SUMMARY OF THE INVENTION

It is therefore the primary object of the present invention to provide novel xanthene compounds.

It is another object of the present invention to provide xanthene compounds useful in photographic products and processes.

It is a further object of the present invention to provide photographic products and processes employing said compounds.

Other objects of this invention will in part be obvious and will in part appear hereinafter.

This invention accordingly comprises the process involving the several steps and the relation and order of one or more of such steps with respect to each of the others and the products and compositions possessing the features, properties and the relation of elements which are exemplified in the following detailed disclosure and the scope of the application of which will be indicated in the claims.

According to the present invention, novel xanthene compounds are provided which possess certain substituted phenyl groups in the 3 and 6 positions; a substituted phenyl moiety in the 9 position which moiety has the formula

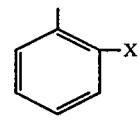

wherein X is

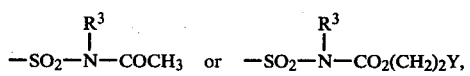

R$^3$ is alkyl and Y is an electron-withdrawing group; and optionally, possess a sulfo group in the 2-position or sulfo groups in the 2- and 7-positions. In another embodiment, photographic products and processes are provided which employ the above-denoted xanthene compounds, which compounds are irreversibly decolorized by forming a new ring-closed compound when contacted with an alkaline photographic processing composition.

For a fuller understanding of the nature and objects of the present invention, reference should be had to the following detailed description taken in conjunction with the accompanying drawings.

DETAILED DESCRIPTION OF THE INVENTION

Figure 1:
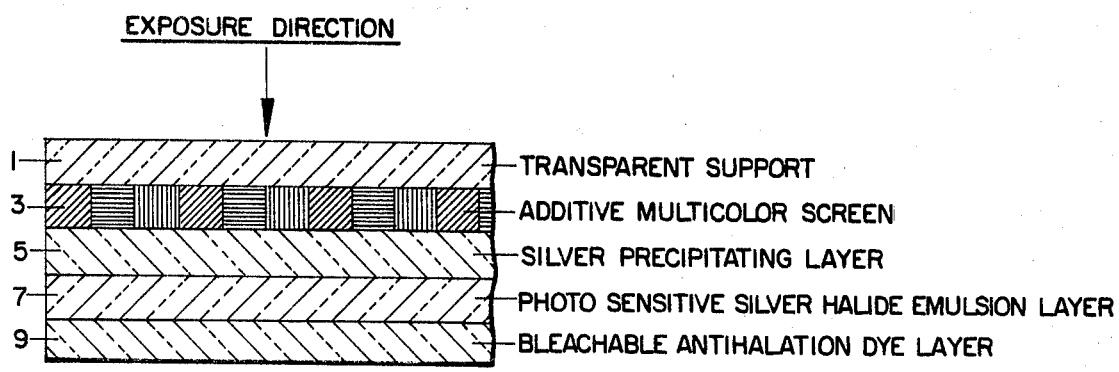
FIG. 1 is a diagrammatic, enlarged cross-sectional view of a diffusion transfer film unit incorporating a xanthene dye of the present invention as a bleachable antihalation dye layer.

Specifically, the compounds employed in accordance with the present invention may be represented by the formulae

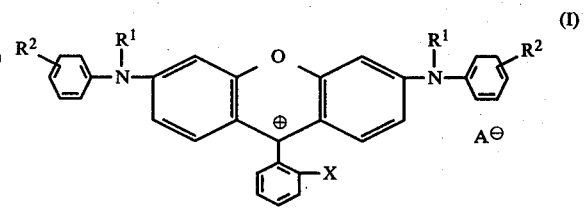

and

-continued

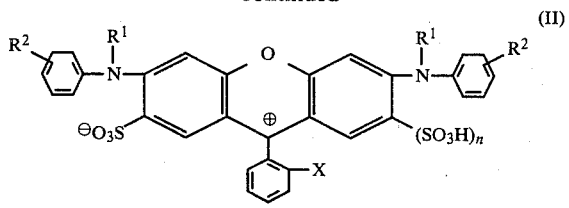
(II)

wherein each $R^1$ the same or different is alkyl, each $R^2$ the same or different is an electron-withdrawing group having a positive sigma value greater than 0.6, X is

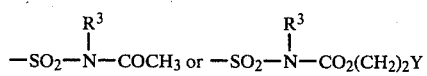

wherein $R^3$ is alkyl and Y is an electron-withdrawing group, n is 0 or 1 and A is an anion, said $R^2$ group being ortho, meta or para to said N atom. Typically said $R^1$ groups are alkyl containing 1 to 7 carbon atoms, e.g., methyl, ethyl, n-propyl, n-butyl, s-butyl, n-hexyl and benzyl, and said $R^3$ groups are alkyl containing 1 to 4 carbon atoms. Usually the $R^1$ groups are the same, and the $R^2$ groups are the same.

The electron-withdrawing group, Y, preferably has a positive sigma value ($\sigma^-$) greater than 0.6. Preferred electron-withdrawing groups for both Y and said $R^2$ include nitro; cyano;

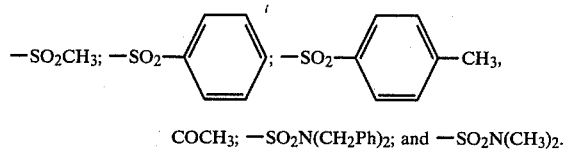

$COCH_3$; $-SO_2N(CH_2Ph)_2$; and $-SO_2N(CH_3)_2$.

The sigma value for these and other groups, such as, $-CHO$, $-COOH$, $-COOC_2H_5$ and $-CONH_2$ have been reported by Eugen Müller, Methoden Der Organischem Chemie, Georg Thieme Verlag, Stuttgart, 1970, p. 78 in terms of $\sigma^-$ values based on the ionization of p-substituted phenols.

The anion associated with the subject xanthenes compounds, i.e., A in formula I above may be any of the simple anions, for example, tosylate, sulfate, nitrate, perchlorate, methane sulfonate, methane hydrogen disulfonate, m-benzene hydrogen disulfonate, acetate, oxalate or halide, such as, chloride or bromide.

The compounds of formula II are substituted with one and preferably two sulfo groups thereby eliminating the "floating", i.e., external anion $A^\ominus$. In addition, the presence of two such groups enhances the dispersibility of the dye in binder materials coated from aqueous dispersions, and the second sulfo group may be used as a mordanting group with certain polymeric binders to prevent migration of the dye in the photographic product.

Preferred xanthene compounds of the present invention are the compounds of Formulae I and II wherein said X is

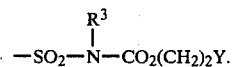

It should be understood that other resonance forms of the subject compounds are intended to be encompassed by Formulae I and II.

As noted above, the subject compounds are initially colored, i.e., capable of absorbing visible radiation, and at an alkaline pH, are converted to a colorless product by undergoing an irreversible cleavage reaction with base. The colorless product formed is a new compound which is different from and non-reversible to the colored compound by a change in pH. In particular, it is the X group substituted on the phenyl moiety that undergoes the irreversible cleavage reaction in alkaline solution that is complete within a predetermined time at a predetermined alkaline pH to give the new colorless compound, namely, the cyclic sulfonamide, as illustrated by the following wherein X is

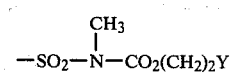

and A is $Br^\ominus$.

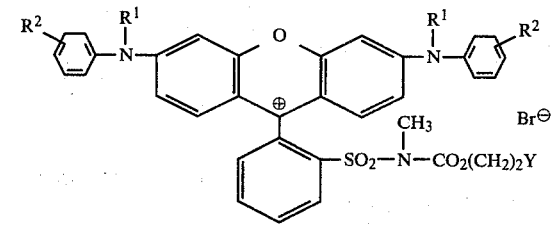

colored $\downarrow OH^\ominus$

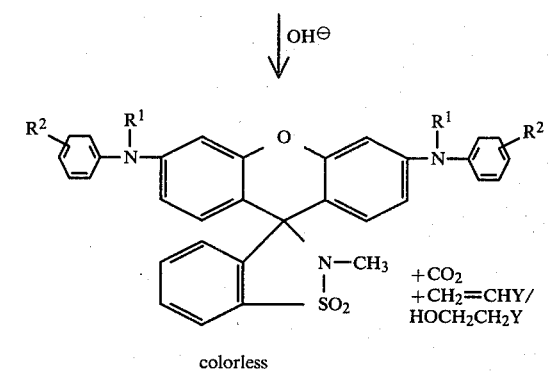

colorless

Where X is $$-SO_2-N(R^3)-COCH_3,$$

the cleavage by-product is $$\overset{O}{\underset{\ominus}{\|}}OCCH_3.$$

It will be appreciated that the sulfonated compounds of formula II undergo cleavage in the same manner and that the by-products formed upon cleavage of the X group are colorless. Because the said cleavage reaction proceeds at a faster rate at higher pH's, the subject compounds are particularly suitable for use in photographic processes, where the pH is maintained above about 10 at least for the time necessary for decolorization to the corresponding ring-closed product.

The xanthene dyes of the present invention may be prepared, for example, (a) by reacting a compound of the formula

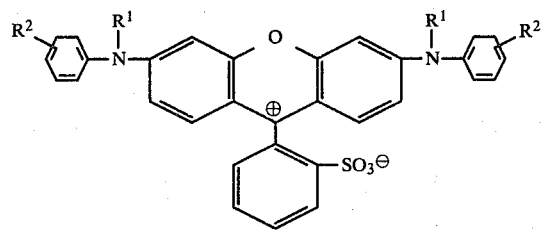

wherein each $R^1$ the same or different is alkyl and each $R^2$ the same or different is an electron-withdrawing group having a positive sigma value greater than 0.6 with phosphorus pentachloride or thionyl chloride to give the corresponding sulfonyl chloride of the formula

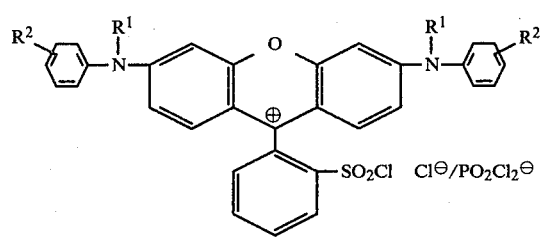

wherein $R^1$ and $R^2$ have the same meaning given above;

(b) reacting said sulfonyl chloride with ammonia to give the corresponding cyclic sulfonamide of the formula

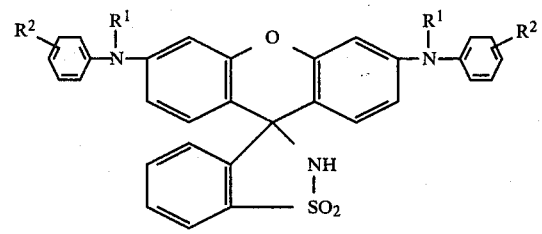

wherein $R^1$ and $R^2$ have the same meaning given above;

(c) reacting said cyclic sulfonamide with an alkylating agent to give the corresponding N—$R^3$ sulfonamide of the formula

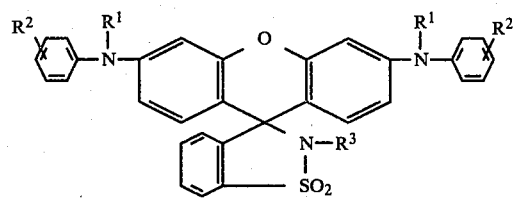

wherein $R^3$ is alkyl and $R^1$ and $R^2$ have the same meaning given above;

(d) reacting said N—$R^3$ sulfonamide with a reducing agent to give the corresponding reduction product of the formula

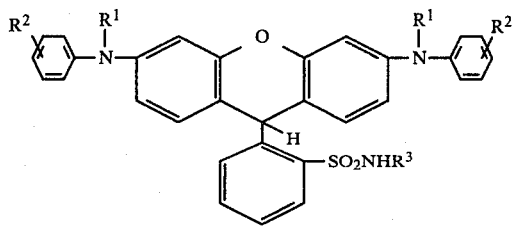

wherein $R^1$, $R^2$ and $R^3$ have the same meaning given above;

(e) reacting said reduction product with the appropriate acylating agent, for example, $ClCOCH_3$ or $ClCO_2(CH_2)_2Y$ to give the leuco dye precursor of the formula

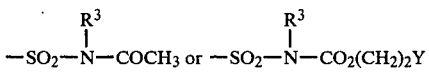

wherein X is $$-SO_2-\overset{R^3}{\underset{|}{N}}-COCH_3 \text{ or } -SO_2-\overset{R^3}{\underset{|}{N}}-CO_2(CH_2)_2Y$$

wherein Y is an electron-withdrawing group and $R^1$, $R^2$ and $R^3$ have the same meaning given above; and (f) oxidizing said leuco dye precursor preferably using o-chloranil as the oxidizing agent followed by isolating the dye product from its o-chloranil complex with an acid to yield the dye product.

To synthesize the sulfo-substituted xanthene compounds, the leuco dye precursor of step (e) is reacted with chlorosulfonic acid in a solvent, such as, methylene chloride to give mainly the monosulfonated product or in a more polar solvent, such as, acetic anhydride to give essentially the disulfonated product of the formulae

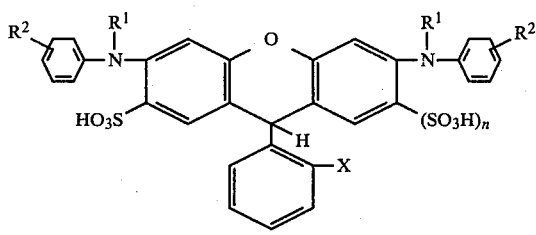

wherein $R^1$, $R^2$ and X have the same meaning given above and n is 0 or 1. This sulfonated leuco dye precursor is then oxidized in the same manner as described in step (f) above.

The starting materials for use in step (a) may be prepared, for example, (1) by reacting sulfonefluorescein dichloride with a substituted aniline,

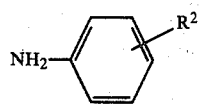

wherein $R^2$ is an electron-withdrawing group having a positive sigma value greater than 0.6 to give the mono-substituted sulfonefluorescein compound of the formula

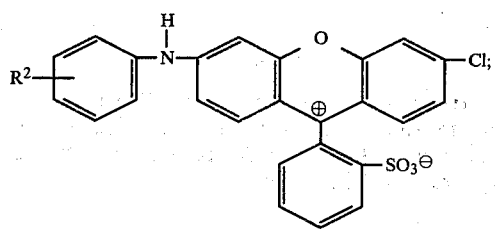

(2) reacting the mono-substituted compound of step (1) with a substituted aniline,

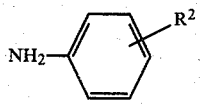

wherein $R^2$ is an electron-withdrawing group having a positive sigma value greater than 0.6 to replace the other chloro group and give the compound of the formula

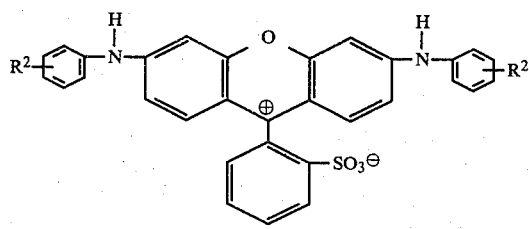

wherein said $R^2$ groups may be the same or different; and (3) reacting the compound of step (2) with an alkylating agent to substitute one of said N atoms with an alkyl group and then reacting the compound thus obtained with a second alkylating agent to substitute the other said N atom with a different alkyl group or reacting the compound of step (2) with an alkylating agent to substitute both of said N atoms with alkyl groups, the same. Where the $R^2$ substituent(s) of the N,N-dialkylated compound are alkylthio, the compound of step (3) is then converted to the corresponding alkylsulfonyl-substituted compound before converting to the sulfonyl chloride as in step (a) above.

Where said $R^2$ groups are the same, both chloro groups of the sulfonefluorescein dichloride starting material may be replaced in a single step, but preferably, they are replaced in a stepwise fashion as shown above.

The acylating agent may be prepared in a conventional manner, for example, by reacting the selected carboxylic acid, such as $R''COOH$, with phosphorus trichloride, phosphorus pentachloride or thionyl chloride to give the corresponding $R''COCl$, or by reacting the selected $HO(CH_2)_2Y$ with phosgene to give the corresponding $ClCO_2(CH_2)_2Y$.

The following examples are given to further illustrate the present invention and are not intended to limit the scope thereof.

EXAMPLE 1

Preparation of the compound having the formula

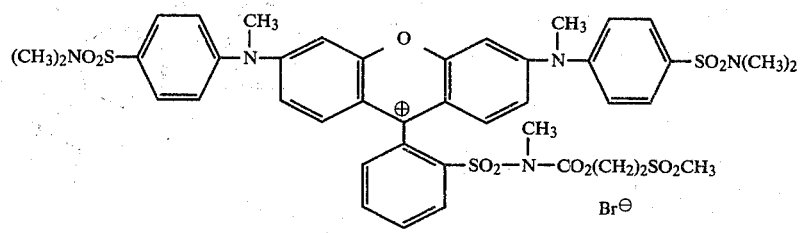

(a) A mixture of 10.0 g (0.05 M) of sulfonefluorescein dichloride

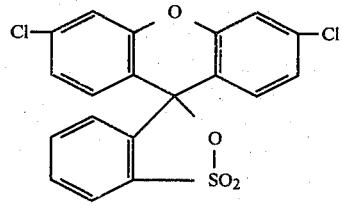

and 20.26 (0.05 M) of p-(N,N-dimethylsulfonamido)aniline in 160 ml of 2-methoxyethyl ether were stirred together for 24 hours, filtered, washed with a small amount of 2-methoxyethyl ether, then with ether and dried in vacuo to give 18.53 g of the compound (b) The above compound, 20.0 g (35.1 mM) and 14.1 g (70.3 mM) of p-(N,N-dimethylsulfonamido)aniline and 20 ml 1-methyl-2-pyrrolidinone were heated in an oil bath at 170° C. under an atmosphere of nitrogen for 4 hours. The deep magenta mixture was then treated with 100 ml 1-methyl-2-pyrrolidinone, cooled to room temperature and poured into a solution of 200 ml conc. HCl and 1400 ml water. This mixture was centrifuged, and the residue was washed with saturated sodium chloride solution and placed in a crystallizing dish to air dry over the weekend. The residue, which contained a considerable amount of sodium chloride, was then dried under vacuum at (70° C.) for 4 hours to give 25.4 g of crude material comprising the compound

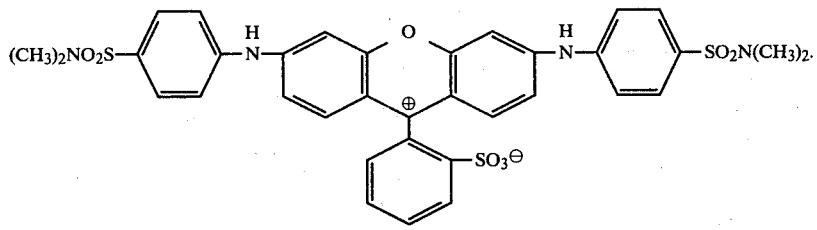

(c) The compound prepared in step (b), 25.4 g, (34.7 mM) was dissolved in 300 ml dry dimethylsulfoxide. (Some solid material was observed floating in the solution which was probably sodium chloride.) A 50% sodium hydride dispersion, 6.72 g, was added to the above solution all at once and then allowed to stir at room temperature for 1½ hours. The green solution was cooled in an ice bath and iodomethane (300 g) was added dropwise over a period of about one hour. The mixture was allowed to warm to room temperature overnight with stirring. The mixture was poured into three liters of water containing 200 ml conc. HCl and extracted with methylene chloride (6×200 ml). The combined methylene chloride extracts were washed with a 2 N HCl solution (5×1000 ml) and dried over sodium sulfate. The solvent was removed in vacuo to give 10.41 g of the compound

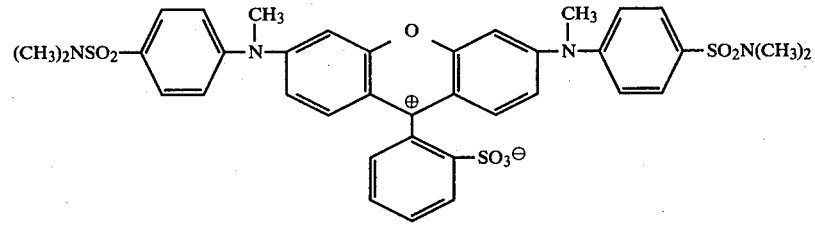

(d) The compound prepared in step (c), 10.4 g (about 13.7 mM), was dissolved in 150 ml of chloroform and treated with 6.25 g (30 mM) of phosphorus pentachloride. The resulting mixture was heated at reflux for 5 hours and then allowed to stir at room temperature overnight. The purple solution was transferred to a separatory funnel, washed with water (2×75 ml) and then dried over magnesium sulfate. The mixture was filtered to remove the magnesium sulfate and the filtrate cooled in an ice bath. The filtrate comprised the sulfonyl chloride of the formula

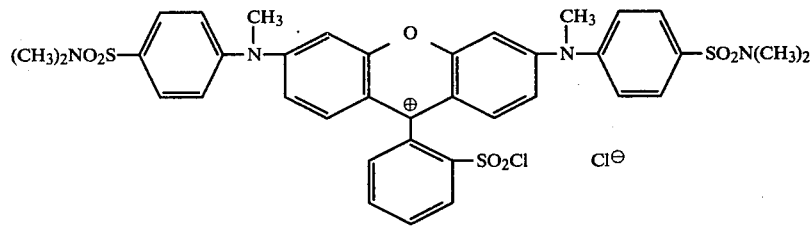

(e) Ammonia gas was bubbled into the filtrate obtained in step (d) until saturated. It was then allowed to come to room temperature and stirred overnight. (The purple color of the solution became much less intense.) The mixture was filtered to remove the salts, and the solvent removed from the filtrate in vacuo leaving 10.67 g of residue. The residue was taken up in 25 ml chloroform:methanol (100:1), applied to medium pressure liquid chromatography column and eluted with 1000 ml chloroform:methanol (100:1), then with chloroform:methanol (50:1). Fractions 2 to 7 were combined and the separation repeated eluting with chloroform:methanol (100:1) to give 5.0 g (90–95% purity) of the compound

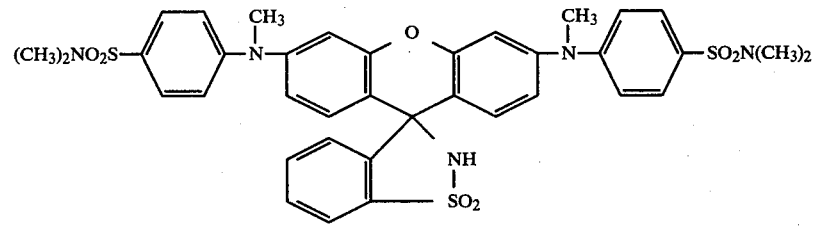

(f) The compound prepared in step (e), 4.85 g (6.4 mM) was dissolved in 60 ml of dry 2-methoxyethyl ether. To this solution, 0.88 g (7.9 mM) of potassium-t-butoxide was added all at once and the resulting solution allowed to stir at room temperature for one hour. The dark mixture was cooled in an ice bath and 0.75 ml (1.0 g; 7.9 mM) of dimethylsulfate was added all at once. The mixture was allowed to come to room temperature overnight and then was poured into 600 ml of water containing 30 g of sodium chloride. The mixture was stirred for about 15 minutes, filtered and the product washed with water. The product was taken up in about 100 ml of methylene chloride, washed with saturated sodium chloride solution (2×75 ml) and dried over sodium sulfate. Methylation did not go to completion so the methylation was repeated on the dried material which was dissolved in 60 ml dry 2-methoxyethyl ether and then treated with 0.95 g (8.47 mM) of potassium-t-butoxide. This mixture was heated for one hour at 50°, then cooled in an ice bath. The mixture was then treated with 0.80 ml (1.068 g; 8.47 mM) of dimethyl sulfate. The resulting reaction mixture was allowed to come to room temperature and stirred for 5 days. The mixture was poured into 600 ml water containing 30 g of sodium chloride and allowed to stir for 15 minutes. The reaction product was filtered, washed with water and dissolved in approximately 100 ml of methylene chloride. The methylene chloride solution was washed with saturated sodium chloride solution and then dried over sodium sulfate. The solvent was removed to give 3.7 g of the compound

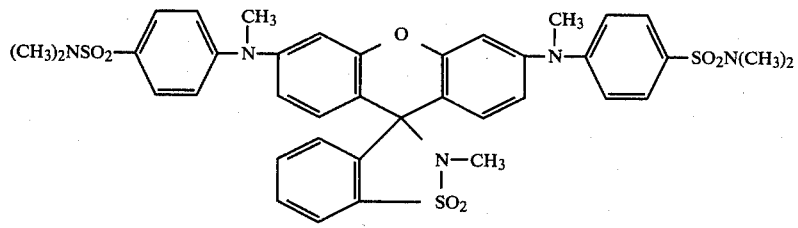

(g) The compound prepared in step (f), 774 mg (1.0 mM) was suspended in 20 ml glacial acetic acid. To this suspension was added 261 mg zinc dust (4.0 mg-atoms), and the mixture was heated in a water bath at approximately 50° C. under an atmosphere of nitrogen. (TLC after 3 hours showed the presence of some starting material.) Another 261 mg of zinc dust was added, the mixture heated at about 60° C. for 2 hours and then allowed to cool to room temperature overnight under an atmosphere of nitrogen. (TLC showed no starting material.) The mixture was poured into 100 ml water with stirring for 15 minutes, filtered, washed with water and dried in vacuo. The residue was dissolved in methylene chloride, filtered to remove any unreacted zinc dust and salts, and the solvent removed in vacuo to give 0.8 g of the compound

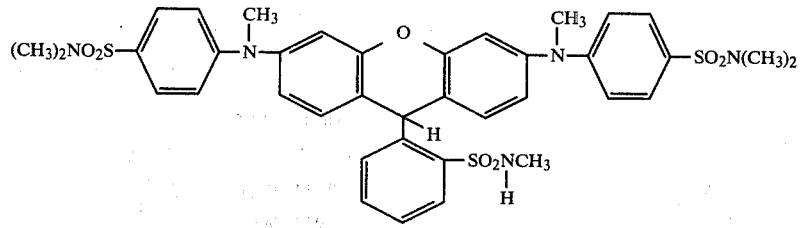

(h) The compound prepared in step (g), 0.80 g (1.0 mM) in 10 ml dry pyridine was treated with 746 mg (4.0 mM) of ClCO$_2$(CH$_2$)$_2$SO$_2$CH$_3$ under an atmosphere of nitrogen overnight. The mixture was poured into 100 ml water with stirring and extracted with chloroform (3×25 ml). The combined chloroform extracts were washed with 1 N HCl solution (3×25 ml), saturated sodium chloride (1×25 ml) and dried over sodium sulfate. The solvent was stripped in vacuo to give 0.92 g of the leuco dye precursor of the formula

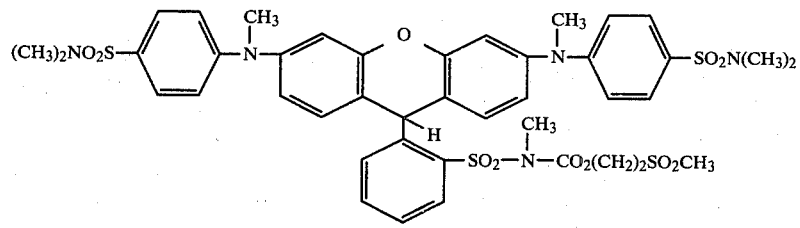

(i) The leuco dye precursor, 2.9 g (3.13 mM), in 150 ml of methylene chloride was treated with 1.15 g (4.7 mM) of o-chloranil with stirring overnight. The mixture was concentrated to 50 ml, cooled in an ice bath, and then hydrogen bromide gas was bubbled into the cold solution until it was saturated. Then the solution was allowed to come to room temperature, poured into 650 ml ether with stirring for 15 minutes. The product was filtered, washed with ether and 1.8 g of the title compound was purified by medium pressure liquid chromatography using 8.5% methanol/methylene chloride solvent. λmax 568, epsilon 76,000 (in ethanol).

EXAMPLE 2

Preparation of the compound having the formula

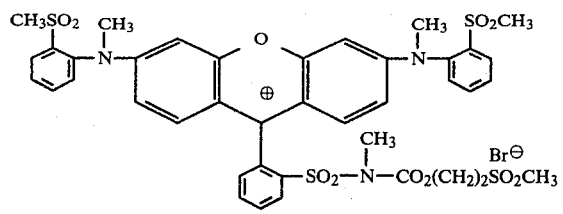

(a) A mixture of 68.9 g (0.17 M) of sulfonefluorescein dichloride, 50 g (0.36 M) 2-methylthioaniline and 7.26 g (0.18 M) magnesium oxide in 135 ml of dimethyl sulfoxide was heated at 140°–145° C. under nitrogen with stirring for 2.5 hours and then poured into 1500 ml of 2 N hydrochloric acid with vigorous stirring. The mixture was stirred for about one hour, the crude reaction product filtered, washed voluminously with water and dried in vacuo overnight to give 94.9 g of solid comprising the compound of the formula

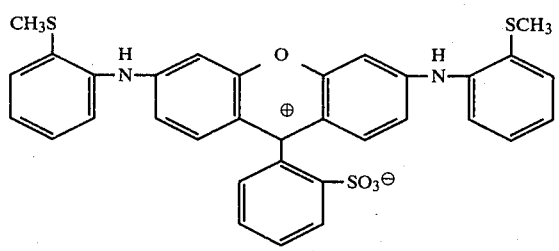

(b) To a mixture of 50 g (0.082 M) of the compound prepared in step (a) in 500 ml of dimethyl sulfoxide under an atmosphere of nitrogen was added 19.65 g of 50% sodium hydride (previously washed with hexane; ≡9.82 g, 0.41 M). The resulting mixture was allowed to stir at room temperature for two hours, and then 100 g (0.70 M) of iodomethane was added dropwise to the green solution. The mixture turned magenta in color within minutes. The mixture was allowed to stir at room temperature over the weekend, then poured into 6000 ml 2 N hydrochloric acid, stirred for approximately one-half hour and filtered. The filter cake was treated with approximately 1200 ml of methylene chloride, washed with 1 N hydrochloric acid (4×500 ml), ½-saturated sodium chloride solution (1×500 ml) and then dried over magnesium sulfate. The solvent was evaporated under reduced pressure leaving 57.67 g of crude reaction product. High pressure liquid chromatography of the crude product gave 20.47 g of the compound having the formula

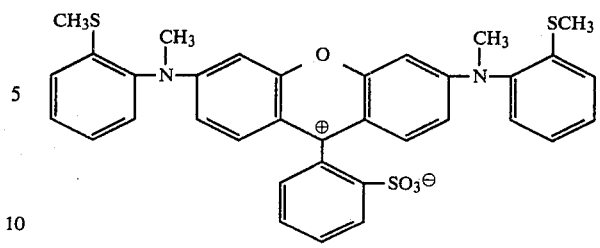

Overall yield from sulfonefluorescein was 35% by weight.

A 1.0 g sample was dissolved in a minimum amount of methylene chloride, precipitated in about 100 ml of ether, and the precipitate filtered and dried in vacuo. (Ethanol: λmax 543 nm—Epsilon 98,000).

(c) A solution of 10.0 g (15.7 mM) of the compound of step (b) in 75 ml methylene chloride was added dropwise to a solution of 20.2 g of 80–90% m-chloroperoxybenzoic acid (equivalent to 16.2–18.2 g) in 400 ml methylene chloride. The temperature increased from 18° to 32° C. The mixture was allowed to stir at room temperature overnight. The mixture was then filtered to remove a small amount of m-chlorobenzoic acid. The filtrate was washed with 10% aqueous sodium hydrogen sulfite (3×250 ml), 5% aqueous sodium bicarbonate (3×250 ml), ½-saturated sodium chloride solution (2×250 ml) and dried over magnesium sulfate. The solvent was evaporated under reduced pressure, and the residue dried under high vacuum for about one hour to give 9.7 g of the compound of the formula

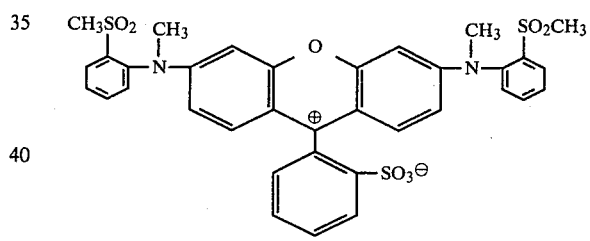

(Ethanol: λmax 534 nm—Epsilon 105,000).

(d) To a solution of 17.89 g (24.45 mM) of the compound of step (c) dissolved in 400 ml of chloroform was added 10.6 g (50.9 mM) of phosphorus pentachloride. The resulting mixture was heated at reflux for 6 hours, then allowed to come to room temperature overnight. The reaction product comprising the compound of the formula

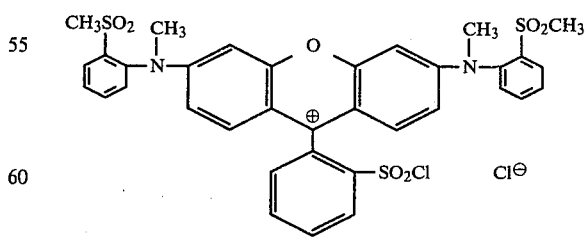

was used directly in the next step without isolation from the reaction mixture.

(e) The reaction mixture of step (d) was cooled to about 5° C. in an ice-bath. Then anhydrous NH₃ gas was bubbled into the mixture until it was saturated. The temperature rose from 5° to 22° C. The ice-bath was removed and the reaction mixture allowed to warm to room temperature. After 6 hours of stirring, the mixture was filtered to remove the salts. The filtrate was washed with water containing a little sodium chloride (3×200 ml) and then dried over anhydrous sodium sulfate. The solvent was evaporated under reduced pressure to give 18.58 g of crude product, which was further purified by high pressure liquid chromatography to yield 15.27 g of the compound of the formula

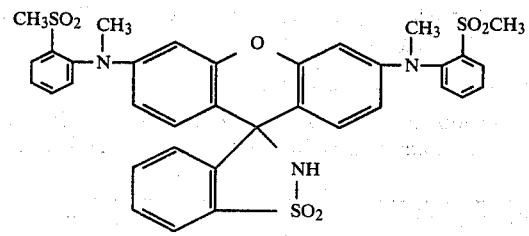

as a light pink solid.

A 1.0 g sample of this compound was crystallized from ethanol containing a little NH$_3$ gas to give 0.45 g of light pink solid. When this solid was dissolved in methanol and added to buffer solutions having a pH of 4, 5, 6 and 7, respectively, the compound was colored at pH 4 and pH 5 but was colorless at pH 6 and pH 7.

(f) To a mixture of 0.50 g (0.71 mM) of the compound of step (e) in 10 ml methylene chloride and 0.75 ml of 1.0 N sodium hydroxide (0.75 mM) in 10 ml water was added 232 mg (≡197.3 mg; 0.71 mM) of 85% tetra-n-butylammonium chloride and 0.25 ml (≡568; 4.0 mM) of iodomethane. After about 45 minutes the reaction appeared to be essentially complete. (TLC showed no starting material.) The reaction was allowed to stir overnight, and the TLC looked the same. The methylene chloride layer was separated and washed with water (5×25 ml), dried over sodium sulfate and the solvent evaporated leaving 0.57 g of the reaction product which was crystallized from about 5 ml of ethanol to give the compound of the formula

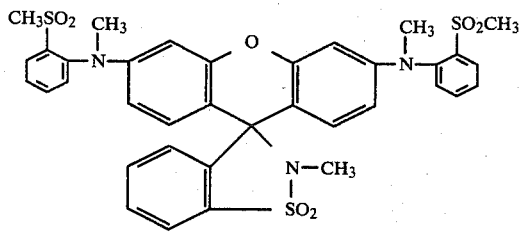

When a solution of this compound in methanol was added to buffer solutions having a pH of 4, 5, 6 and 7, respectively, the compound was colored at pH 4 but was colorless at pH's 5, 6 and 7.

(g) A solution of 11.71 g (16.35 mM) of the compound of step (f) in 150 ml glacial acetic acid was treated with 3.2 g (49 mg-atoms) of zinc dust under an atmosphere of nitrogen in a water bath at approximately 50° C. for about 8 hours, then at room temperature over the weekend. (TLC's of aliquots were taken periodically and showed varying amounts of starting material even after 8 hours.) The mixture was poured into 1500 ml water with stirring. The precipitate was filtered, washed with water and treated with methylene chloride (about 300 mls). The methylene chloride solution was filtered, washed with water (about 100 ml) and dried over sodium sulfate. The solvent was evaporated in vacuo yield 11.35 g (97%) of the compound of the formula

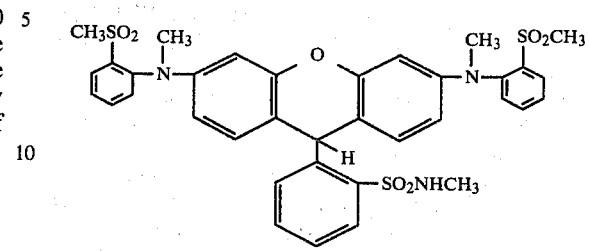

(h) A mixture of 10.4 g (14.5 mM) of the compound of step (g) in 125 ml dry pyridine was treated with 10.8 g (58 mM) of ClCO$_2$(CH$_2$)$_2$SO$_2$CH$_3$. The mixture was stirred at room temperature under an atmosphere of nitrogen overnight. (TLC of an aliquot showed no starting material, only a single spot corresponding to the leuco dye.) The mixture was poured into 1400 ml water and the precipitated reaction product filtered, washed with water and dried in vacuo to give 10.74 g of the compound of the formula

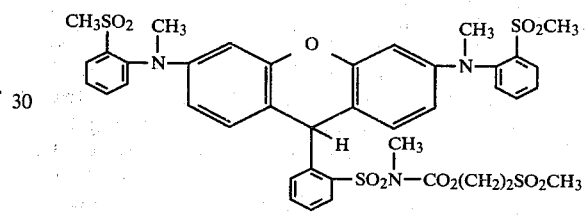

as a light pink solid.

(i) A solution of 721 mg (0.83 mM) of the compound of step (h) in 15 ml methylene chloride was treated with 393 mg (1.6 mM) of o-chloranil. The mixture was allowed to stir at room temperature until TLC showed no starting material. The mixture was cooled in an ice-bath, then saturated with HBr gas. The mixture was allowed to warm to room temperature, then poured into 250 ml ether. The crude product was filtered, washed voluminously with ether and dried in vacuo to yield 0.86 g of solid. The solid was purified using medium pressure liquid chromatographic techniques with 12% methanol in chloroform. The fractions corresponding to the major component were combined, the solvent evaporated under reduced pressure and the residue dissolved in a minimum amount of methylene chloride. The methylene chloride solution was added to 100 ml ethyl ether and the precipitated product was filtered, washed with ether and dried in vacuo to yield 392 mg of the title compound. (Ethanol: λmax 550 nm—Epsilon 96,000).

Step (i) was repeated as follows:

To a solution of 4.0 g (4.6 mM) of the compound of step (h) dissolved in 100 ml methylene chloride was added 2.26 g (9.2 mM) of o-chloranil all at once. The resulting mixture was allowed to stir at room temperature until TLC showed no starting material present (about one hour). The mixture was cooled in an ice-bath, then saturated with anhydrous HBr gas. The mixture was allowed to warm to room temperature during one hour and then poured into 1000 ml ether. The precipitated product was filtered, washed with ether and dried in vacuo to give 4.69 g of the title compound. (Ethanol: λmax 548 nm—Epsilon 99,800).

Calculated for N$_3$O$_{11}$S$_4$C$_{40}$H$_{40}$Br: C: 50.73; H: 4.26; N: 4.44; S: 13.55; Br: 8.44. Calculated for N$_3$O$_{11}$S$_4$C$_{40}$H$_{40}$Br.2HBr: C: 43.33; H: 3.82; N: 3.79; S: 11.57; Br: 21.62. Found—C: 43.67; H: 3.56; N: 3.60; S: 11.31; Br: 19.09.

To free the dye product of the .2HBr indicated to be present by the elemental analysis, a 0.50 g sample of the dye was dissolved in 20 ml methylene chloride and washed with 5% aqueous sodium bicarbonate solution (3×20 ml). The methylene chloride was dried over sodium sulfate to yield 0.49 g of solid that was further purified by medium pressure liquid chromatography. The purified material had a λmax=550 nm and an Epsilon=101,000 as measured in ethanol. Elemental analysis of the purified dye for N$_3$O$_{11}$S$_4$C$_{40}$H$_{40}$Br was as follows:

Calculated—C: 50.73; H: 4.26; N: 4.44; S: 13.55: Br: 8.44. Found—C: 49.65; H: 4.35; N: 4.29; S: 11.76; Br: 8.59.

Steps (a) and (b) also were carried out as follows using ethylene glycol rather than dimethyl sulfoxide/magnesium oxide in the condensation of 2-methylthioaniline with sulfonefluorescein dichloride.

(a) A mixture of 10.0 g (24.6 mM) of sulfonefluorescein dichloride and 12.4 ml (d 1.111; 13.8 g, 99 mM) of 2-methylthioaniline in 100 ml ethylene glycol was heated under an atmosphere of nitrogen at 160° C. for 7 hours. The mixture was poured into 1000 ml 1 N hydrochloric acid solution with stirring. After stirring for about 30 minutes the precipitated product was filtered, washed with water, a little acetone and then air-dried overnight. This dried material (15.2 g) was continuously extracted with acetone for about 24 hours, then dried in vacuo to give 13.4 g of the corresponding 3,6-bis-(2'-methylthioanilino)sulfonefluorescein.

(b) To a 1000 ml three-necked flask equipped with overhead stirrer, nitrogen inlet-outlet tube and dropping funnel was placed 12.0 g (19.65 mM) of the compound of step (a) and 400 ml of dry dimethyl sulfoxide under an atmosphere of nitrogen. To this solution, 3.78 g of 50% NaH (≡1.89 g; 78.6 mM), previously washed with hexane, as added all at once. The mixture gradually became dark green in color. After two hours, 5.9 ml (13.5 g; 95 mM) of iodomethane was added dropwise to the above solution. (The mixture gradually became magenta in color.) This mixture was allowed to stir over the weekend. The mixture was then poured into 4000 ml of 2 N hydrochloric acid solution and allowed to stir for about one-half hour. The precipitated product was filtered, washed with water and then dissolved in methylene chloride (approx. 500 ml). The methylene chloride solution was washed with 2 N hydrochloric acid solution (2×250 ml), dried over magnesium sulfate and the solvent evaporated under reduced pressure to give 19.5 g of crude reaction product. The crude material (18.0 g) was purified by high pressure liquid chromatography to give 11.06 g of the N-methylated 3,6-bis-(2'-methylthioanilino)sulfonefluorescein. (Ethanol: λmax 543 nm—Epsilon 105,000). Overall yield from the sulfonefluorescein was 78% by weight.

The methylation of step (b) also was carried out in KOH/dimethyl sulfoxide and also in NaH/dimethyl sulfate as follows:

(b) A solution of 11.77 g (16.77 mM) of the compound of step (e) in 150 ml dry 2-methoxyethyl ether was treated with 0.85 g (≡0.425 g; 17.6 mM) of 50% NaH under an atmosphere of nitrogen. The mixture was allowed to stir at room temperature for one hour, then treated with 1.75 ml (≡2.333 g; 18.5 mM) of dimethyl sulfate. TLC of an aliquot removed after 3 hours showed some starting material present. Another 0.21 g of 50% NaH was added and the mixture allowed to stir for one hour. Then 0.40 ml of dimethyl sulfate was added. TLC of an aliquot removed after another hour showed no starting material, only product. The mixture was poured into 1500 ml water containing 75 g sodium chloride for 15 minutes. The precipitated product was filtered, washed voluminously with water and air-dried to give 11.71 g of product.

EXAMPLES 3 TO 6

Compounds identical to that of Example 2 except for different counter-ions, i.e., compounds of the formula

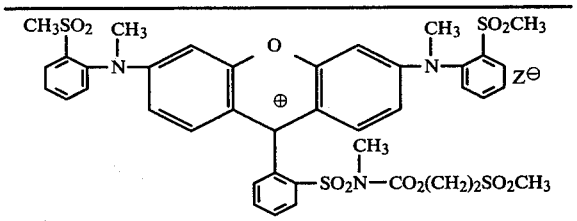

| | |
|---|---|
| wherein Z$^\ominus$ = HSO$_4^\ominus$ | Example 3 |
| CH$_2$⟨SO$_3^\ominus$ / SO$_3$H | Example 4 |
| ⟨SO$_3^\ominus$ / SO$_3$H⟩ | Example 5 |
| CH$_3$SO$_3^\ominus$ | Example 6 | were prepared from the leuco dye precursor designated Compound L having the formula

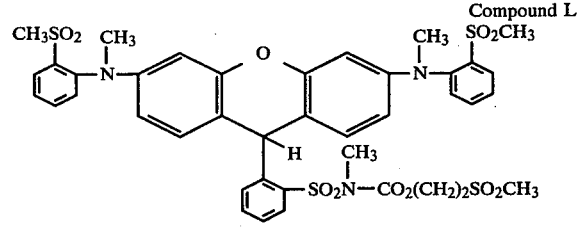

Compound L as described below.

A solution of 100 mg (0.115 mM) of Compound L dissolved in 2 ml glacial acetic acid was treated with 56.6 mg (0.23 mM) of o-chloranil. TLC after 1.5 hours showed no starting material. Two drops of conc. sulfuric acid were added and the mixture was allowed to stir for one hour, then poured into 20 ml ether. The precipitated product was filtered, washed with ether and air-dried to give the compound of Example 3. (Ethanol: λmax 550 nm—Epsilon 96,000).

A solution of 100 mg (0.115 mM) of Compound L dissolved in 2 ml glacial acetic acid was treated with 56.6 mg (0.23 mM) of o-chloranil. Two drops of methane-disulfonic acid were added after 1.5 hours. The mixture was allowed to stir for one hour, poured into 20 ml ether and the precipitated product filtered. The product was washed with ether and air-dried to give the compound of Example 4. (Ethanol/H₂O: νmax 550 nm—Epsilon 96,000).

A solution of 200 mg (0.23 mM) of Compound L dissolved in 4 ml glacial acetic acid was treated with 113 mg (0.46 mM) of o-chloranil. TLC after 1.5 hours showed no starting material. 109.6 mg (0.46 mM) of m-benzenedisulfonic acid was added all at once, stirring continued for one-half hour and the reaction mixture poured into 50 ml ether. The precipitated product was filtered, washed with ether and dried in vacuo to give 200.5 mg of the compound of Example 5. (Ethanol: νmax 550 nm—Epsilon 82,000, approx.).

A solution of 0.5 g (0.58 mM) of Compound L dissolved in 15 ml methylene chloride was treated with 283 mg (1.15 mM) of o-chloranil added all at once. TLC after 1.5 hours showed no starting material. Then the mixture was cooled in an ice-bath and 11 ml of methanesulfonic acid was added. The mixture was stirred for 30 minutes in the cold, one hour at room temperature and then poured into 200 ml ether. The precipitated product was filtered, washed with ether and dried to give 552 mg of the compound of Example 6. (Ethanol νmax 550 nm—Epsilon 94,000; H₂O: νmax 547 nm—Epsilon 93,000).

EXAMPLE 7

Preparation of the compound of the formula

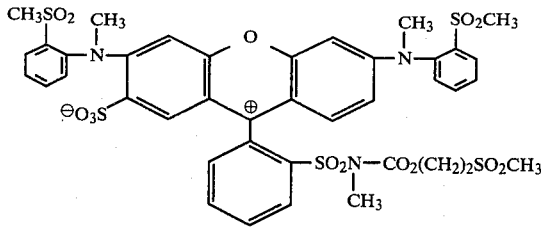

A solution of 500 mg (0.58 mM) of Compound L dissolved in 10 ml dry methylene chloride was treated with a solution of 0.084 ml of chlorosulfonic acid (≡147 mg; 1.2 mM) in 5 ml methylene chloride. A precipitate formed immediately. This mixture was allowed to stir at room temperature overnight. The methylene chloride was decanted and the residue was washed with methylene chloride. TLC showed the presence of a considerable amount of starting material.

The residue (0.567 g; 0.598 mM) was dissolved in approximately 10 ml methanol, treated with 294 mg (1.2 mM) of o-chloranil and heated at reflux for 30 minutes, then at room temperature for 2 hours. The precipitate was filtered, and the filtrate evaporated under reduced pressure (about 200 mg). The filtrate was treated using preparative TLC techniques to give 96 mg of single spot material corresponding to the monosulfonated dye product, i.e., the title compound (soluble in chloroform; slightly soluble in methanol; insoluble in water). The title compound, when incorporated into a layer of a graft copolymer of 4-vinylpyridine and vinylbenzyl-trimethylammoniumchloride grafted on hydroxyethyl cellulose in a weight ratio of 2.2/1/2.2, respectively, had a νmax of 568 nm.

EXAMPLE 8

Preparation of the compound of the formula

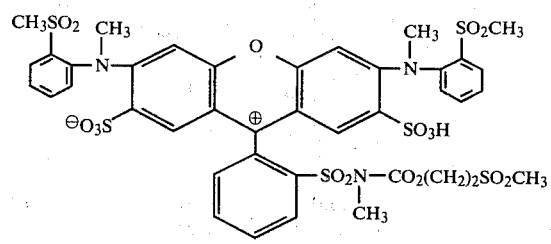

A solution of 500 mg (0.57 mM) of Compound L dissolved in 5 ml acetic anhydride was treated with 0.084 ml (≡147 mg; 1.2 mM) of chlorosulfonic acid dropwise under an atmosphere of nitrogen. No precipitate had formed after 4 hours. The mixture was allowed to stir at room temperature overnight. Then the mixture was poured into 50 ml ether. The precipitate was filtered, washed with ether and dried in vacuo to give 0.56 g of solid. TLC of this solid showed the disulfonated product, i.e., the title compound to be the major product.

Sulfonefluorescein dichloride was prepared as follows:

In a 5 liter 3-necked round-bottom flask equipped with a paddle stirrer, a reflux condenser and a thermometer was placed 1.5 liters of ethyl acetate which was then cooled to 0° C. using an ice bath. Sulfonefluorescein (250 g) was added followed by 200 ml of thionyl chloride. The temperature rose slightly. The temperature was allowed to fall back to 0° C. 750 ml of N,N-dimethylformamide (DMF) was then added all at once. The temperature rose to about 30° C. After the additions were completed, the mixture was stirred for 1 hour. The ice bath was removed to allow the temperature of the reaction mixture to rise to room temperature after which the mixture was placed on a steam bath and heated to reflux with stirring. During heating the mixture became lighter in color and thicker. (The color was brown.) After refluxing 10 to 15 minutes the reaction mixture was placed in an ice bath and cooled to 0° C. with stirring continuing. The cold reaction mixture was filtered and washed with cooled 15% DMF/ethyl acetate solution until the color of the precipitate became as light as possible, then washed with ether. After sucking under a rubber dam, the sulfonefluorescein dichloride was air dried. Yield 184.3 g (68%); 99.7% pure by L.C.

The new ring-closed cleavage products formed when the subject compounds undergo irreversible cleavage in aqueous alkaline solution have the formulae

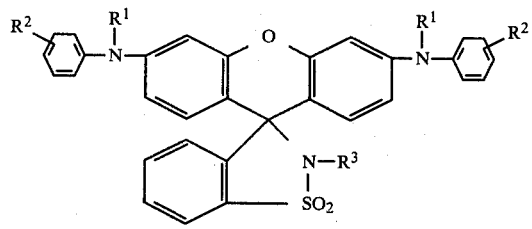

and

-continued

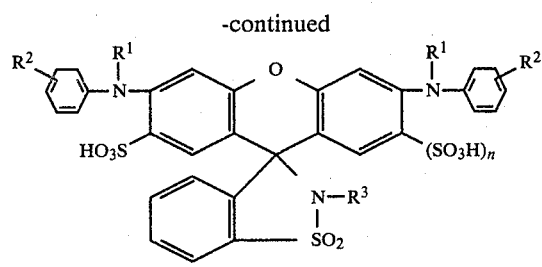

wherein $R^1$, $R^2$, $R^3$ and n have the same meaning given above. Though the alkyl substituent on the N atom of the X group is not essential to give a cleavage product that remains colorless as the pH is reduced, it is desirable to so substituted said N atom to increase the epsilon of the uncleaved dye to give a more highly colored compound.

Methanolic solutions of cleavage products of the subject compounds designated compounds A and B below and methanolic solutions of compounds C to G having the structures set forth below were added to a series of buffered solutions having a pH of 4, 5, 6 and 7, respectively, in order to determine the approximate pH at which the compounds become colored as the pH drops below alkaline values. The results are given in Table I below.

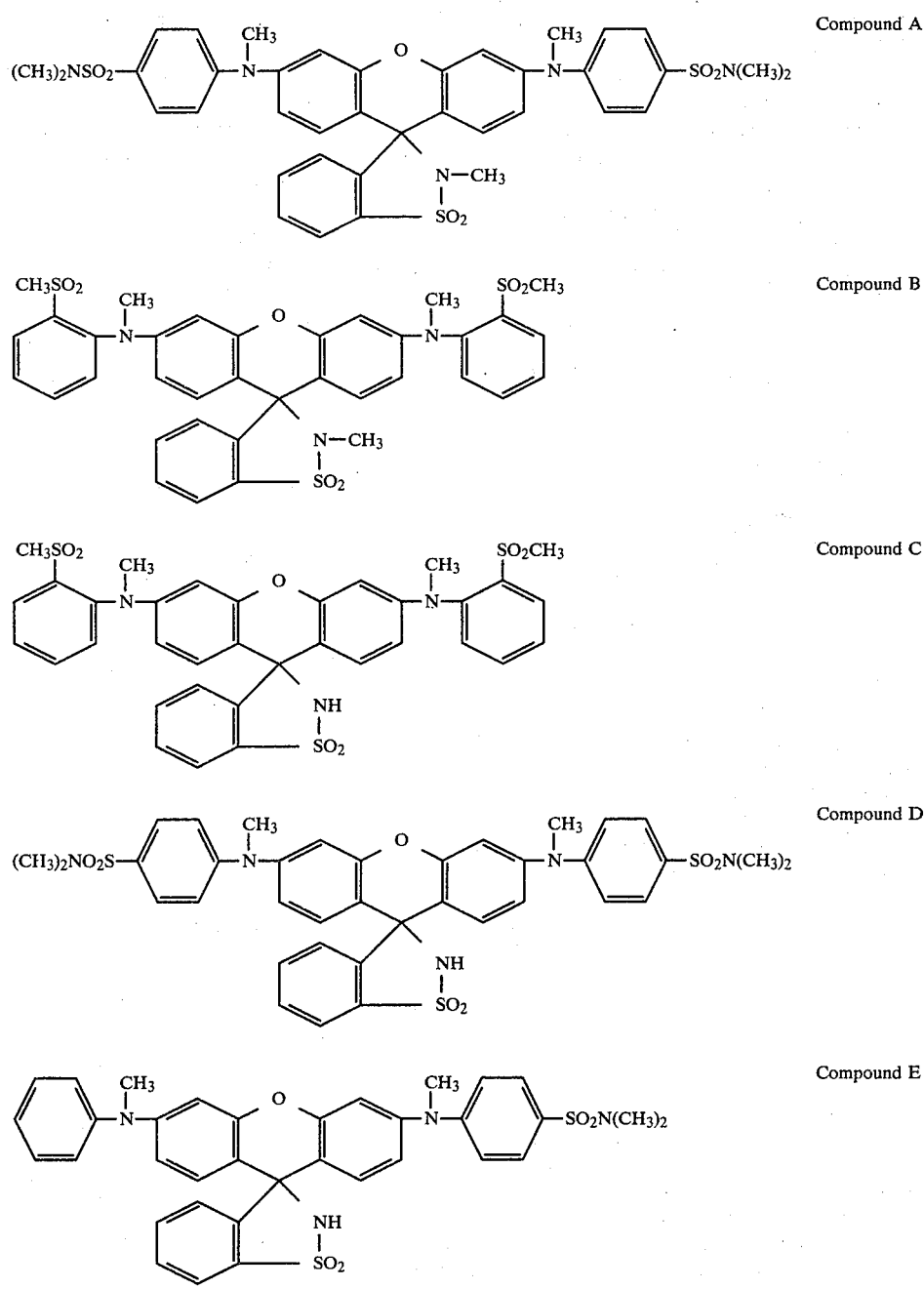

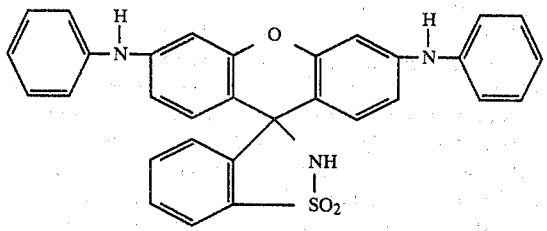

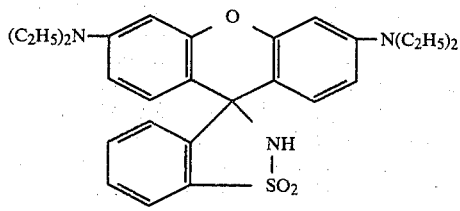

Compound F

Compound G

TABLE I

| Compound | pH 4 | pH 5 | pH 6 | pH 7 |
|---|---|---|---|---|
| A | + | o | o | o |
| B | + | o | o | o |
| C | + | + | o | o |
| D | ++ | o | o | o |
| E | ++ | + | + | o |
| F | ++ | + | + | o |
| G | +++ | +++ | ++ | + |

+++ = very intense color
++ = intense color
+ = faint color
o = no color

It will be readily apparent from reference to Table I that the cleavage products of the subject dyes (Compounds A and B) were colorless at pH 5 and were only faintly colored at pH 4 and that Compound D also was colorless at pH 5 and Compound B only faintly colored at pH 5. In comparison, Compounds E and F were faintly colored at pH 6 and became intensely colored at pH 4. Compound G was faintly colored at pH 7 becoming very intensely colored as the pH was reduced to pH 4.

From this data, it can be seen that placing an electron-withdrawing substituent on both of the 3,6 N-phenyl groups give xanthene compounds whose cleavage products remain colorless down to about pH 4.5 whereas similar xanthene compounds without an electron-withdrawing substituent on the N-phenyl groups or with only one such substituted N-phenyl group give cleavage products that do not remain colorless much below pH 7. Besides being colored at pH 7, the cleavage products of N,N-dialkyl compounds are even more intensely colored at the lower pH's.

As noted previously, the dyes of the present invention have the ability to decolorize completely and irreversibly in base by undergoing an irreversible cleavage reaction within a predetermined time at a predetermined pH to give a new colorless compound which remains colorless at the pH's normally encountered during processing subsequent to "bleaching" so that the new compound may be retained in a photographic film unit, e.g., a photosensitive element without the possibility of color reappearing in time. Typically, dyes may be selected for use as antihalation dyes, e.g., in a non-light-sensitive layer positioned intermediate a photosensitive silver halide emulsion layer and the support. Also, dyes may be selected for use as color correction filter dyes where absorption of light within a particular wavelength range during exposure is desirable for achieving appropriate color balance.

Illustrative film units in which the dyes of the present invention may be advantageously used as antihalation dyes are described, for example, in British Pat. No. 1,482,156. These film units comprise, in the order in which incident light passes therethrough, an additive multicolor screen, a photosensitive silver halide emulsion layer, an antihalation layer in which the selected compound may be disposed, and preferably, an image-receiving layer. As described therein, exposure of the silver halide layer is accomplished through the screen which possesses optical filter elements selectively transmitting predetermined portions of incident radiation, e.g., red, green and blue light, to the underlying photosensitive silver halide layer. Upon photographic processing with an aqueous alkaline processing composition, soluble silver complex is transferred by diffusion and deposited in a superposed image-receiving layer as a function of the degree of exposure of silver halide behind each filter element. The silver image thus formed may then serve to modulate the quantity of light passing through the filter elements in the reverse direction during projection through a transparent support.

In a preferred embodiment, the image-receiving layer is intermediate the photosensitive silver halide emulsion layer and the additive multicolor screen and remains in position as part of an integral film unit prior to, during and after formation of the image. The antihalation dye is disposed in a processing composition permeable layer adjacent to the photosensitive layer on the side opposite the screen and serves to prevent the reflection or backscattering of incident light which has passed through the photosensitive layer thereby eliminating the exposure of silver halide grains in the photosensitive layer other than those within the intended photoexposure path.

As noted above, the dyes of the present invention also are useful as color correction filter dyes in photographic film units comprising multilayered, multicolor photosensitive elements employing a blue-, a green- and a red-sensitive silver halide layer, and particularly in integral negative-positive diffusion transfer film units wherein the image-receiving layer carrying the color transfer image is not separated from the developed photosensitive layers after processing but both components are retained together as a permanent laminate. Included as part of the laminate is a layer of light-reflecting material, preferably titanium dioxide, positioned between the image-carrying layer and the developed photosensitive layer(s). The light-reflecting layer separating the image-carrying and photosensitive components provides a white background for the transfer image and masks the developed photosensitive layer(s). In addition to these layers, the laminate usually includes dimensionally stable outer layers or supports, at least one of which is transparent so that the resulting transfer image may be viewed by reflection against the background provided by the light-reflecting layer.

Illustrative of patents describing such film units are U.S. Pat. No. 2,983,606 issued Mar. 9, 1961 to Howard G. Rogers, U.S. Pat. Nos. 3,415,644, 3,415,645 and 3,415,646 issued Dec. 10, 1968 to Edwin H. Land, U.S. Pat. Nos. 3,594,164 and 3,594,165 issued July 20, 1971 to Howard G. Rogers, and U.S. Pat. No. 3,647,437 issued Mar. 7, 1972 to Edwin H. Land. Copending U.S. patent application Ser. No. 537,124 of Edwin H. Land is concerned with multicolor diffusion transfer film units, wherein a layer of a dye, preferably a dye bleachable by the processing composition, is so positioned that photoexposure is effected therethrough, whereby said dye layer is effective as a color correction filter. For convenience, the specification of this application is specifically incorporated herein.

Whether used as antihalation dyes, color correction filter dyes or in other conventional photographic light-screening applications, the dyes of the present invention when disposed in a processing composition-permeable layer are completely and irreversibly decolorized by contacting with an aqueous alkaline processing composition for the time necessary for converting the colored dye compound to the new colorless ring-closed compound. The time required for decolorization, i.e., for conversion of the colored compound to the colorless product via said irreversible cleavage reaction may be measured at any given alkaline pH, and for a selected decolorization time, the pH of the processing composition contacted with and remaining in contact with the colored filter dye should be at least as high as that predetermined to give the selected decolorization time. In terms of $T\frac{1}{2}$, the preferred compounds have a half-life ($T\frac{1}{2}$) in approximately 1 N NaOH of about 30 seconds or less. By $T\frac{1}{2}$ is meant the time measured for one-half of said colored dye to decolorize.

The dyes of the present invention may be incorporated into the appropriate layer of the photographic film unit using any of the techniques known in the art. For instance, the selected compound can be dissolved in the appropriate solvent and then dispersed, in the presence of a wetting agent if desired, in a coating solution containing a hydrophilic colloid binder, e.g., gelatin, and the resulting coating solution applied as the desired layer, for example, coated on a transparent support to provide an antihalation layer, or coated over the outermost photosensitive layer of a multilayered, multicolor photosensitive element to provide a color correction filter layer through which photoexposure is made. The concentration of compound in the layer will vary depending upon the product in which the filter layer is to be used and may be readily determined empirically to provide the optical density necessary for the specific use. It will be appreciated that the dyes of the present invention may be used in combination with each other and also may be used in combination with other classes of dyes previously employed in antihalation, color correction and other filter layers.

FIG. 1 of the accompanying drawing, which illustrates one embodiment of the present invention, is an enlarged cross-sectional view of an integral diffusion transfer film unit comprising a transparent film base or support 1 carrying on one surface, in order, additive multicolor screen 3 comprising a plurality of primary red color filter elements, a plurality of primary green color filter elements and a plurality of blue color filter elements arranged in a geometrically repetitive distribution in side-by-side relationship in substantially a single plane, photoinsensitive layer 5 carrying silver precipitating nuclei, photosensitive layer 7 containing silver halide crystals and antihalation layer 9 containing one or more light-screening dyes of the present invention.

As discussed in aforementioned British Pat. No. 1,482,156, the degree of light absorption of the antihalation layer in such film units can vary over a relatively wide range, but usually, the antihalation layer possesses a transmission density range from about 0.4 to 1.4. Preferably, the transmission density is greater than 0.6 so that in the event a plurality of film units is employed in a stacked relationship during photoexposure, the antihalation layer will have sufficient density, i.e., light-absorbing capacity to substantially prevent reflectance as well as prevent exposure of underlying film units.

In determining the appropriate light-absorbing capacity for cyan, magenta and yellow for color correction purposes, "color compensating" filters as conventionally used in front of the camera lens may be employed in the usual manner as a convenient method of approximating the type and quantity of filtration which it would be desirable to provide. A layer containing the appropriate color correction dye(s) in a corresponding density may then be provided as a layer through which photoexposure is to be made.

Multicolor diffusion transfer images may be obtained using a variety of arrangements of the image-receiving layer and the silver halide emulsions. Thus, these layers may be carried by a common support brought into superposition after photoexposure. A particularly advantageous film structure is shown in U.S. Pat. No. 3,415,644 wherein the requisite layers are in superposed relationship prior to and during photoexposure, and these layers are maintained in superposed relationship as a permanent laminate after processing and image formation. Such film units typically contain an outer transparent layer or support through which photoexposure is effected and the final multicolor image viewed, and another outer layer or support carrying at least the photosensitive layers, the latter support being opaque. While these supports or sheet-like elements may simply be held in superposed relationship, e.g., by a binding tape around the edges, in the preferred embodiment these elements are laminated together prior to photoexposure. This prelamination provides a number of benefits, both during manufacture and in photoexposure. Following exposure, the elements are delaminated by the distribution of a fluid processing composition which, upon solidification, bonds the elements together to form the desired permanent laminate. Procedures for forming such prelaminated film units wherein the two elements are temporarily laminated together prior to exposure are described, for example, in U.S. Pat. No. 3,625,231 to Albert J. Bachelder and Frederick J. Binda, and U.S. Pat. No. 3,652,282 to Edwin H. Land, both issued Mar. 28, 1972 and in U.S. Pat. No. 3,793,023 issued to Edwin H. Land on Feb. 19, 1974.

Figure 2:
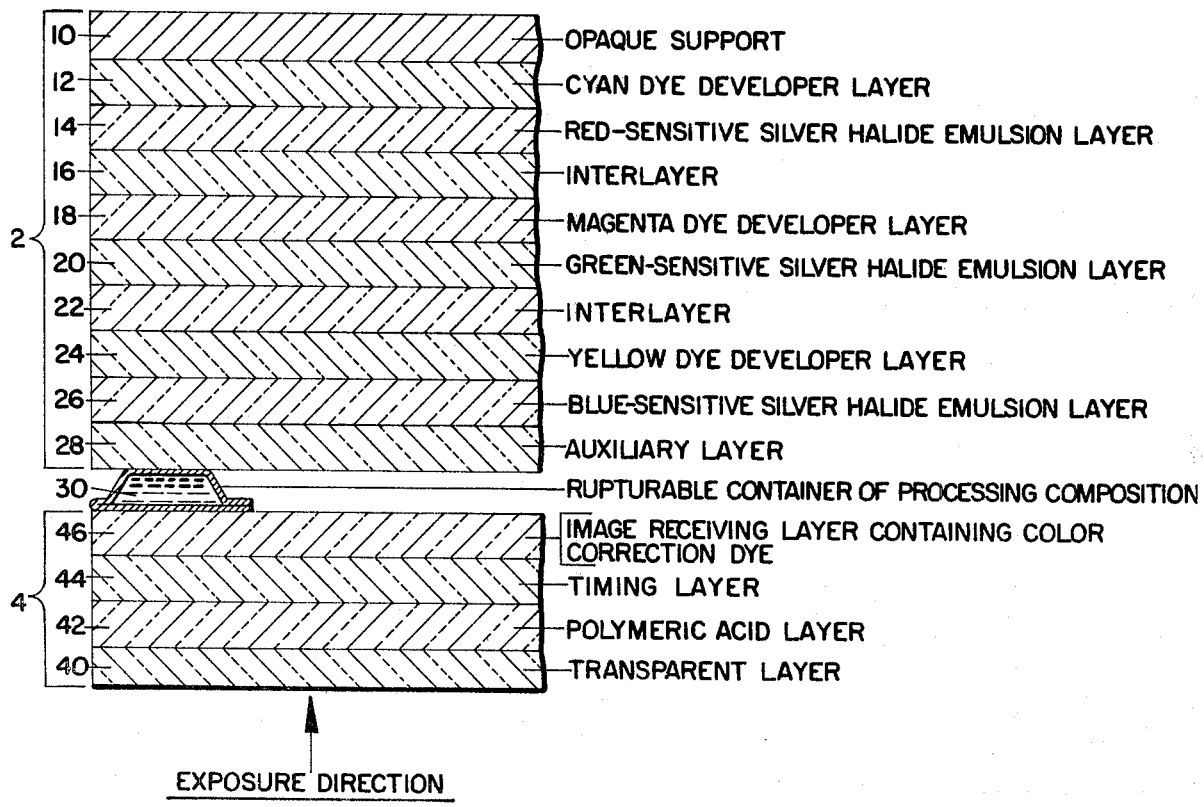
FIG. 2 is a diagrammatic, enlarged cross-sectional view of another diffusion transfer film unit incorporating a xanthene dye of the present invention as a color correction filter dye in the image-receiving layer.

Further description of this embodiment of the present invention may be facilitated by reference to FIG. 2 of the accompanying drawing which illustrates a diffusion transfer film unit adapted to provide integral negative-positive reflection prints and employing dye developers as the image dyes.

FIG. 2 illustrates a diffusion transfer film unit comprising a photosensitive element or component 2, a rupturable container 30, and an image-receiving element or component 4. The photosensitive element 2 comprises an opaque support 10 carrying, in turn, a cyan dye developer layer 12, a red-sensitive silver halide emulsion layer 14, an interlayer 16, a magneta dye developer layer 18, a green-sensitive silver halide emulsion layer 20, an interlayer 22, a yellow dye developer layer 24, a blue-sensitive silver halide emulsion layer 26, and an auxiliary layer 28. The positive or image-receiving element 4 comprises a transparent support 40 carrying, in turn, a polymeric acid layer 42, a timing layer 44 and an image-receiving layer 46 having dispersed therein a bleachable, light-screening dye of this invention as a color correction filter dye. The two elements are held in superposed, registered relationship, e.g., by a binding tape (not shown), so that photoexposure of the silver halide emulsion layers is effected through image-receiving layer 46 containing the bleachable dye. The rupturable container 30 contains a processing composition and is so positioned that, upon rupture the processing composition is distributed between the superposed elements 2 and 4. By including in the processing composition a light-reflecting pigment, preferably titanium dioxide, a light-reflecting layer may be provided against which the transfer image formed in the image-receiving layer 46 may be viewed. The developed photosensitive layers are masked from view by the light-reflecting layer and remain with the receiving layer 46 as part of a permanent laminate. The rupturable container 30 is of the type shown in U.S. Pat. No. 2,543,181 and is positioned adjacent the leading edge of the film unit.

In the processing of the film unit, the film unit is advanced relative to and between a pair of pressure-applying members which apply compressive pressure to the rupturable container 30 to eject its liquid contents between the photosensitive and image-receiving components 2 and 4 and then distribute the mass of liquid between the sheets toward the trailing ends thereof to form a layer of substantially uniform, predetermined thickness at least co-extensive with the image area. In order to insure sufficient processing liquid to form a layer of the required area and thickness between the sheets, excess processing liquid may be provided in container 30 and trapping means (not shown) provided for collecting and retaining excess processing liquid overrun. Details of the various layers of this and of the film unit of FIG. 1 may be found in the herein cited patents and applications and need not be recited here.

Processing of film units of the type described in FIG. 2 is initiated by distributing the processing composition between predetermined layers of the film unit. In exposed and developed areas, the dye developer will be immobilized as a function of development. In unexposed and undeveloped areas, the dye developer is unreacted and diffusible, and this provides an imagewise distribution of unoxidized dye developer, diffusible in the processing composition, as a function of the point-to-point degree of exposure of the silver halide layer. The desired transfer image is obtained by the diffusion transfer to the image-receiving layer of at least part of this imagewise distribution of unoxidized dye developer. In the illustrated embodiment, the pH of the photographic system is controlled and reduced by the neutralization of alkali after a predetermined interval, in accordance with the teachings of the above noted U.S. Pat. No. 3,615,644, to reduce the alkalinity to a pH at which the unoxidized dye developer is substantially insoluble and non-diffusible. As will be readily recognized, the details of such processes form no part of the present invention but are well known; the previously noted U.S. patents may be referred to for more specific discussion of such processes.

Multicolor images may be obtained by providing the requisite number of differentially exposable silver halide emulsions, and said silver halide emulsions are most commonly provided as individual layers coated in superposed relationship. Film units intended to provide multicolor images comprises two or more selectively sensitized silver halide layers each having associated therewith an appropriate image dye-providing material providing an image dye having spectral absorption characteristics substantially complementary to the light by which the associated silver halide is exposed. The most commonly employed negative components for forming multicolor images are of the "tripack" structure and contain blue-, green-, and red-sensitive silver halide layers each having associated therewith in the same or in a contiguous layer a yellow, a magenta and a cyan image dye-providing material respectively. Interlayers or spacer layers may, if desired, be provided between the respective silver halide layers and associated image dye-providing materials or between other layers. Integral multicolor photosensitive elements of this general type are disclosed in U.S. Pat. No. 3,345,163 issued Oct. 3, 1967 to Edwin H. Land and Howard G. Rogers as well as in the previously noted U.S. patents, e.g., in FIG. 9 of the aforementioned U.S. Pat. No. 2,983,606.

A number of modifications of the structures described in connection with FIG. 2 will readily suggest themselves to one skilled in the art. Thus, for example, the multicolor multilayer negative may be replaced by a screen-type negative as illustrated in U.S. Pat. No. 2,968,554 issued Jan. 17, 1961 to Edwin H. Land and in the aforementioned U.S. Pat. No. 2,983,606 particularly with respect to FIG. 3 thereof.

The image dye-providing materials which may be employed in such processes generally may be characterized as either (1) initially soluble or diffusible in the processing composition but are selectively rendered non-diffusible in an imagewise pattern as a function of development; or (2) initially insoluble or non-diffusible in the processing composition but which are selectively rendered diffusible or provide a diffusible product in an imagewise pattern as a function of development. These materials may be complete dyes or dye intermediates, e.g., color couplers. The requisite differential in mobility or solubility may, for example, be obtained by a chemical action such as a redox reaction or a coupling reaction.

As examples of initially soluble or diffusible materials and their application in color diffusion transfer, mention may be made of those disclosed, for example, in U.S. Pat. Nos. 2,774,668; 2,968,554; 2,983,606; 3,087,817; 3,185,567; 3,230,082; 3,345,163; and 3,443,943. As examples of initially non-diffusible materials and their use in color transfer systems, mention may be made of the materials and systems disclosed in U.S. Pat. Nos. 3,185,567; 3,719,489; 3,443,939; 3,443,940; 3,227,550; 3,227,552; and 4,076,529. Many types of image dye-providing substances and film units useful therewith also are discussed in the aforementioned U.S. Pat. No. 3,647,437 to which reference may be made.

It is also to be understood that "direct positive" silver halide emulsions may also be used, depending upon the particular image dye-providing substances employed and whether a positive or negative color transfer image is desired.

A preferred opacification system to be contained in the processing composition to effect processing outside of a camera is that described in the above-mentioned U.S. Pat. No. 3,647,437, and comprises a dispersion of an inorganic light-reflecting pigment which also contains at least one light-absorbing agent, i.e., optical filter agent, at a pH above the pKa of the optical filter agent in a concentration effective when the processing composition is applied, to provide a layer exhibiting optical transmission density > than about 6.0 density units with respect to incident radiation actinic to the photosensitive silver halide and optical reflection density > than about 1.0 density units with respect to incident visible radiation.

In lieu of having the light-reflecting pigment in the processing composition, the light-reflecting pigment used to mask the photosensitive strata and to provide the background for viewing the color transfer image formed in the receiving layer may be present initially in whole or in part as a preformed layer in the film unit. As an example of such a preformed layer, mention may be made of that disclosed in U.S. Pat. No. 3,615,421 issued Oct. 26, 1971 and in U.S. Pat. No. 3,620,724 issued Nov. 16, 1971, both in the name of Edwin H. Land. The reflecting agent may be generated in situ as is disclosed in U.S. Pat. Nos. 3,647,434 and 3,647,435, both issued Mar. 7, 1972 to Edwin H. Land.

The dye developers (or other image dye-providing substances) are preferably selected for their ability to provide colors that are useful in carrying out subtractive color photography, that is, the previously mentioned cyan, magenta and yellow. They may be incorporated in the respective silver halide emulsion or, in the preferred embodiment, in a separate layer behind the respective silver halide emulsion. Thus, a dye developer may, for example, be in a coating or layer behind the respective silver halide emulsion and such a layer of dye developer may be applied by use of a coating solution containing the respective dye developer distributed, in a concentration calculated to give the desired coverage of dye developer per unit area, in a film-forming natural, or synthetic, polymer, for example, gelatin, polyvinyl alcohol, and the like, adapted to be permeated by the processing composition.

Dye developers, as noted above, are compounds which contain the chromophoric system of a dye and also a silver halide developing function. By "a silver halide developing function" is meant a grouping adapted to develop exposed silver halide. A preferred silver halide development function is a hydroquinonyl group. Other suitable developing functions include ortho-dihydroxyphenyl and ortho- and para-amino substituted hydroxyphenyl groups. In general, the development function includes a benzenoid developing function, that is, an aromatic developing group which forms quinonoid or quinone substances when oxidized.

The image-receiving layer may comprise one of the materials known in the art, such as polyvinyl alcohol, gelatin, etc. It may contain agents adapted to mordant or otherwise fix the transferred image dye(s). Preferred materials comprise polyvinyl alcohol or gelatin containing a dye mordant such as poly-4-vinylpyridine, as disclosed in U.S. Pat. No. 3,148,061 and graft copolymers containing 4-vinylpyridine as disclosed in U.S. Pat. No. 3,756,814.

In the various color diffusion transfer systems which have previously been described and which employ an aqueous alkaline processing fluid, it is well known to employ an acid-reacting reagent in a layer of the film unit to lower the environmental pH following substantial dye transfer in order to increase the image stability and/or to adjust the pH from the first pH at which the image dyes are diffusible to a second (lower) pH at which they are not. For example, the previously mentioned U.S. Pat. No. 3,415,644 discloses systems wherein the desired pH reduction may be effected by providing a polymeric acid layer adjacent the dyeable stratum. These polymeric acids may be polymers which contain acid groups, e.g., carboxylic acid and sulfonic acid groups, which are capable of forming salts with alkali metals or with organic bases; or potentially acid-yielding groups such as anhyrides or lactones. Preferably the acid polymer contains free carboxyl groups. Alternatively, the acid-reacting reagent may be in a layer adjacent to the silver halide most distant from the image-receiving layer, as disclosed in U.S. Pat. No. 3,573,043 issued Mar. 30, 1971 to Edwin H. Land. Another system for providing an acid-reacting reagent is disclosed in U.S. Pat. No. 3,576,625 issued Apr. 27, 1971 to Edwin H. Land.

An inert interlayer or spacer layer may be and is preferably disposed between the polymeric acid layer and the dyeable stratum in order to control or "time" the pH reduction so that it is not premature and interferes with the development process. Suitable spacer or "timing" layers for this purpose are described with particularity in U.S. Pat. Nos. 3,362,819; 3,419,389; 3,421,893; 3,455,686; and 3,575,701.

While the acid layer and associated spacer layer are preferably contained in the positive component employed in systems wherein the dyeable stratum and photosensitive strata are contained on separate supports, e.g., between the support for the receiving element and the dyeable stratum; or associated with the dyeable stratum in those integral film units, e.g., on the side of the dyeable stratum opposed from the negative components, they may, if desired, be associated with the photosensitive strata, as is disclosed, for example, in U.S. Pat. Nos. 3,362,821 and 3,573,043. In film units such as those described in the aforementioned U.S. Pat. Nos. 3,594,164 and 3,594,165, they also may be contained on the spreader sheet employed to facilitate application of the processing fluid.

As is now well known and illustrated, for example, in the previously cited patents, the liquid processing composition referred to for effecting multicolor diffusion transfer processes comprises at least an aqueous solution of an alkaline material, for example sodium hydroxide, potassium hydroxide, and the like, and preferably possessing a pH in excess of 12, and most preferably includes a viscosity-increasing compound constituting a film-forming material of the type which, when the composition is spread and dried, forms a relatively firm and relatively stable film. The preferred film-forming materials comprise high molecular weight polymers such as polymeric, water-soluble ethers which are inert to an alkaline solution such as, for example, a hydroxyethyl cellulose or sodium carboxymethyl cellulose. Other film-forming materials or thickening agents whose ability to increase viscosity is substantially unaffected if left in solution for a long period of time also are capable of utilization. The film-forming material is preferably contained in the processing composition in such suitable quantities as to impart to the composition a viscosity in excess of 100 cps, at a temperature of approximately 24° C. and preferably in the order of 100,000 cps to 200,000 cps at that temperature.

In particularly useful embodiments, the transparent polymeric support contains a small quantity of a pigment, e.g., carbon black, to prevent fog formation due to light-piping by internal reflection within the transparent support, and subsequent exiting from the support surface carrying the photographic layers, of actinic light incident upon an edge thereof; such elements are described in Belgian Pat. No. 777,407. The transparent support advantageously may include an ultraviolet light absorber.

For purposes of illustrating the invention, a solution of a sample of the compound of Example 1 was incorporated into the image-receiving layer 3 of an image-receiving component comprising the structures set forth below by mixing the solution of the compound with a solution of the graft copolymer and coating this mixture on top of the timing layer to complete the image-receiving component.

A transparent 4 mil polyethylene terephthalate film base coated with, in succession:

1. as a polymeric acid layer, a mixture of about 9 parts of a partial butyl ester of polyethylene/maleic anhydride copolymer and 1 part of polyvinyl butyral coated at a coverage of about 2,500 mgs./ft.$^2$;

2. a timing layer containing a 14:1 ratio of a 60-30-4-6 tetrapolymer of butylacrylate, diacetone acrylamide, styrene and methacrylic acid and polyvinyl alcohol at a coverage of 500 mgs./ft.$^2$;

3. a graft copolymer of 4-vinylpyridine and vinylbenzyltrimethylammoniumchloride grafted on hydroxyethyl cellulose in a weight ratio of 2.2/1/2.2, respectively, coated at a coverage of 300 mgs./gt.$^2$ to provide an image-receiving layer and containing the selected dye compound at a coverage of 22 mgs./ft.$^2$.

The image-receiving component containing the dye compound was placed on a piece of gelatin coated Mylar, and the transmission densities for red (R), green (G) and blue (B) were recorded on a transmission densitometer. Then several drops of aqueous 1 N KOH were added to the gelatin sheet, and the image-receiving component was lightly pressed against the gelatin sheet to "bleach" the dye compound. After about 60 seconds, the transmission densities were again recorded for red (R), green (G) and blue (B) for the "sandwich". The results are set forth below.

| Transmission Densities | | | | | |
|---|---|---|---|---|---|
| Before Bleaching | | | After Bleaching | | |
| R | G | B | R | G | B |
| .03 | .28 | .01 | .01 | .00 | .00 |

The densitometer was set at 0.00 for R, G, B with two pieces of gelatin coated Mylar in the light beam. The compound of Example 2 also absorbed in the green region when coated in a copolymer layer similar to layer 3 and was decolorized when contacted with an aqueous alkaline processing composition having a pH > 14.

From these results, it can be seen that the subject dyes are effective in absorbing radiation within a certain wavelength range, and when treated with aqueous alkali are "bleached", i.e., decolorized.

It will be appreciated that various solvents may be employed for dispersing the dyes in the image-receiving or other appropriate layer of the photographic product and that useful solvents may be readily selected for a given compound. Also, it will be understood that where the anion may possibly have an adverse effect on the photosensitive material, the dye will be positioned other than in the silver halide emulsion layer(s), and depending upon the mobility of the dye in a given matrix or binder, it may be desirable to employ an immobilizing group or a group that will mordant to the matrix to prevent migration of the dye, particularly, where the photographic product is subjected to conditions of high temperature and high humidity prior to use.

Also, it will be appreciated that in utilizing the subject dyes to correct color balance, for example, in multicolor diffusion transfer photographic film units that a photosensitive element may be exposed to a suitable multicolor step-wedge and diffusion transfer processed with a given processing composition and image-receiving element. The blue, green and red D log E curves of the resulting multicolor transfer image (sample image) are then prepared. Examination of these D log E curves will indicate to one skilled in color photographic sensitometry the manner and extent to which the individual D log E curves depart from the desired curve shape. From this examination, one may determine by routine analysis and experimentation how much filtration would be required of what wavelength range or ranges to obtain a more desirable color balance. The photosensitive element of another film unit, having the identical photosensitive element, image-receiving element and processing composition as used in obtaining the sample image, is then given the same exposure through a conventional color correction filter(s) of the color and density estimated to be necessary to provide the desired changes in the D log E curves of the sample image. The blue, green and red D log E curves of the resulting test multicolor transfer image are then prepared and compared with the sample. While more than one "test" may be required to determine the color filtration most effective to give the desired D log E curve shape changes, such tests may be performed rapidly and easily. When the appropriate color filtration has been determined, a layer containing a color correction dye or dyes absorbing light in appropriate wavelength range(s) is coated on a transparent support at a coverage calculated to provide the requisite density. This "test" color correction dye layer is placed in the exposure path and the previous exposure test repeated. Analysis of the D log E curves of the resulting multicolor transfer image will indicate what changes, if any, should be made in the spectral absorption range and density prior to incorporating a corresponding color correction dye layer into the diffusion transfer film unit.

It will be recognized that effecting photoexposure through a layer containing the subject dye(s) is effective to "filter", i.e., decrease the exposure given to the silver halide layer(s) exposable by light absorbed by said color correction dye(s) and that one or more dyes of the present invention may be used in conjunction with other filter dyes for effecting changes in one, two or all three of the individual red, green and blue H and D curves to achieve the desired color balance. Though the subject dyes find particular utility in diffusion transfer and other photographic film units where it is desired to bleach the dye(s) during processing subsequent to photoexposure through the dye layer(s), the subject dyes also may be employed in diffusion transfer and other film units where the dye is so positioned as not to contribute dye density to the transfer or final image. Where the filter dye layer through which photoexposure has been made is not part of the transfer image, or where the final image is masked from view as in certain integral negative-positive reflection print structures, the "unbleached" filter dye should be non-diffusible to the image-receiving layer containing the transfer image. The requisite non-diffusion character may be provided by the use of a suitable mordant, by the use of long chain "ballast" or "anchor" substituents and/or other art known techniques.

As noted in the above example, in integral diffusion transfer film units, the color correction dye(s) may be incorporated in the image-receiving layer. The choice of location of the color correction dye(s) will depend in large part upon what stage of the manufacturing process the determination is made to incorporate such a color correction dye. As will be readily apparent, provision of the color correction dye(s) in a separate layer has the advantage of permitting modification after the components have fully "matured" and also permits different modification of portions of the same lot of the positive component.

The supports for the various layers may be any of the types known in the art to be useful. In the preferred embodiments wherein an integral negative-positive reflection print is obtained, the supports should be dimensionally stable and may be polyethylene terephthalate or other polymeric film base, as disclosed in the cross-referenced patents.

It will be recognized that the transfer image formed following exposure and processing of film units of the type illustrated in FIG. 2 will be a geometrically reversed image of the subject. Accordingly, to provide geometrically non-reversed transfer images, exposure of such film units should be accomplished through an image reversing optical system, such as in a camera possessing an image reversing optical system utilizing mirror optics, e.g., as described in U.S. Pat. No. 3,447,437 issued June 3, 1969 to Douglas B. Tiffany.

Where the expression "positive image" has been used, this expression should not be interpreted in a restrictive sense since it is used primarily for purposes of illustration, in that it defines the image produced on the image-carrying layer as being reversed, in the positive-negative sense, with respect to the image in the photosensitive emulsion layers. As an example of an alternative meaning for "positive image", assume that the photosensitive element is exposed to actinic light through a negative transparency. In this case, the latent image in the photosensitive emulsion layers will be positive and the dye image produced on the image-carrying layer will be negative. The expression "positive image" is intended to cover such an image produced on the image-carrying layer, as well as transfer images obtained by use of direct positive silver halide emulsions to provide a "positive" image of the photographed subject.

While the usefulness of the subject xanthene dyes has been illustrated as applied to integral diffusion transfer film units where the transfer image is retained with the developed photosensitive element as part of a permanent laminate, it will be understood that the xanthene dyes of this invention also may be used to provide antihalo, color correction or other light filtering layer(s) in diffusion transfer film units where the transfer image, either in silver or in dye, is separated from the developed photosensitive layer(s) subsequent to processing. Though the image dye-providing materials are preferably dye developers, it will be appreciated that other types of image dyes and dye intermediates may be employed to provide the dye transfer image.

Besides their usefulness in diffusion transfer photographic products and processes, the xanthene dyes of the present invention also may be used in filter layers of conventional photographic materials, for example, in antihalation or color correction layers in conventional negatives, and may be disposed in the appropriate layer(s) in an amount sufficient to provide the desired filtering effect. The selection and incorporation of the xanthene dye for the desired filtering effect may be accomplished in a known manner using conventional techniques and is well within the skill of the art. For example, for color correction purposes, the dye(s) selected may absorb light within a specific wavelength range, e.g., blue, green or red light, or within a combination of several wavelength ranges and will be disposed in a layer through which photoexposure is made. Indeed, it may be desirable in a given instance to filter light of two different wavelength ranges in a ratio such that one silver halide emulsion receives more exposure filtration than does another. As in the diffusion transfer film units, the dye(s) selected for color correction are advantageously applied after the photosensitive element has aged to "maturity", i.e., the sensitometry of the photosensitive element as manufactured is no longer changing significantly with time. Where the subject dyes are employed for antihalation purposes, they may be incorporated, for example, in a layer on one or both sides of a support carrying the photosensitive layer(s) and where they are employed as optical filter agents, they will be so positioned as to prevent post-exposure fogging during processing in ambient light without, of course, interfering with imagewise exposure of the photosensitive layer(s) or with viewing of the final image.

Since certain changes may be made in the hereinafter defined subject matter without departing from the scope of the invention herein involved, it is intended that all matter contained in the above description and examples be interpreted as illustrative and not in a limiting sense.

What is claimed is:
1. A compound of the formulae

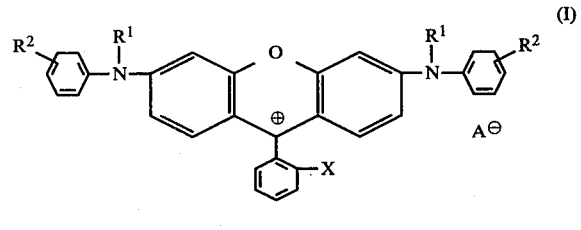

and

-continued

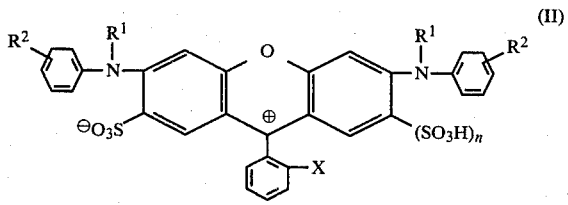

wherein each R¹ the same or different is alkyl; each R² the same or different is an electron-withdrawing group having a positive sigma value (σ−) greater than 0.6 selected from nitro, cyano, —SO₂CH₃,

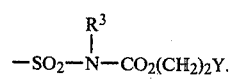

—COOCH₃, —SO₂N(CH₂Ph)₂, —SO₂N(CH₃)₂, —CHO, —COOH, —COOC₂H₅ and —CONH₂; X is $$-SO_2-\underset{R}{N}-COCH_3 \text{ or } -SO_2-\underset{R}{N}-CO_2(CH_2)_2Y$$

wherein R³ is alkyl; Y is an electron-withdrawing group selected from nitro, cyano, —SO₂CH₃,

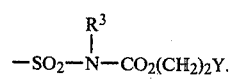

—COOCH₃, —SO₂N(CH₂Ph)₂, —SO₂N(CH₃)₂, —CHO, —COOH, —COOC₂H₅ and —CONH₂; n is 0 or 1; and A is an anion.

2. A compound as defined in claim 1 wherein said R¹ groups are the same.

3. A compound as defined in claim 1 wherein said R² groups are the same.

4. A compound as defined in claim 1 wherein said X is

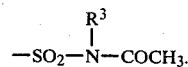

5. A compound as defined in claim 1 wherein X is

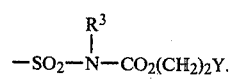

6. The compound

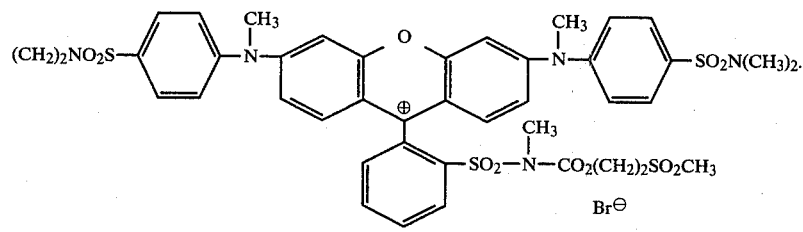

7. The compound

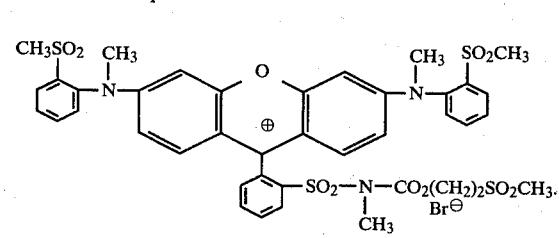

8. The compound

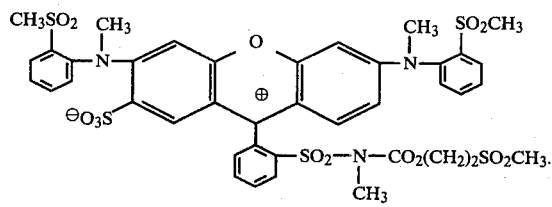

9. The compound

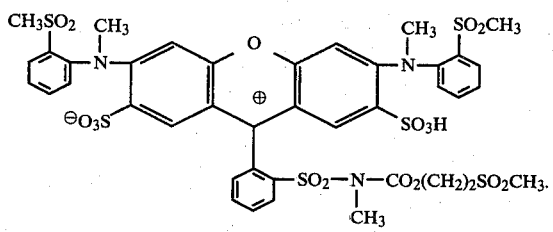

* * * * *